(12) United States Patent
Powell et al.

(10) Patent No.: US 9,181,158 B2
(45) Date of Patent: *Nov. 10, 2015

(54) METHODS FOR CONVERSION OF A GLYCOL REACTION PRODUCT OBTAINED FROM HYDROTHERMAL DIGESTION OF CELLULOSIC BIOMASS SOLIDS INTO A DRIED MONOHYDRIC ALCOHOL FEED

(71) Applicant: SHELL OIL COMPANY, Houston, TX (US)

(72) Inventors: Joseph Broun Powell, Houston, TX (US); Kimberly Ann Johnson, Richmond, TX (US)

(73) Assignee: Shell Oil Company, Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/067,399

(22) Filed: Oct. 30, 2013

(65) Prior Publication Data

US 2014/0128639 A1 May 8, 2014

Related U.S. Application Data

(60) Provisional application No. 61/720,714, filed on Oct. 31, 2012.

(51) Int. Cl.
*C07C 29/60* (2006.01)
*C07C 31/02* (2006.01)
*C10G 3/00* (2006.01)
*C07C 29/132* (2006.01)

(52) U.S. Cl.
CPC .............. *C07C 31/02* (2013.01); *C07C 29/132* (2013.01); *C07C 29/60* (2013.01); *C10G 3/42* (2013.01); *C10G 3/50* (2013.01); *C10G 3/56* (2013.01); *C10G 2300/1011* (2013.01); *C10G 2300/1014* (2013.01); *C10G 2400/02* (2013.01); *C10G 2400/04* (2013.01)

(58) Field of Classification Search
CPC ........................... C07C 29/132; C07C 31/225
See application file for complete search history.

(56) References Cited

U.S. PATENT DOCUMENTS

| | | | |
|---|---|---|---|
| 6,030,915 A | 2/2000 | de Boer | |
| 6,127,229 A | 10/2000 | Chu et al. | |
| 8,262,905 B2 | 9/2012 | Gabrielov et al. | |
| 2008/0216391 A1* | 9/2008 | Cortright et al. | 44/307 |
| 2010/0236988 A1 | 9/2010 | Gabrielov et al. | |
| 2011/0312050 A1* | 12/2011 | Zhang et al. | 435/158 |
| 2012/0151827 A1 | 6/2012 | Powell et al. | |
| 2012/0152836 A1 | 6/2012 | Powell et al. | |
| 2012/0156742 A1 | 6/2012 | Powell et al. | |
| 2012/0167876 A1 | 7/2012 | Qiao et al. | |
| 2012/0317872 A1 | 12/2012 | Powell et al. | |
| 2013/0109896 A1 | 5/2013 | Powell et al. | |
| 2013/0152457 A1 | 6/2013 | Powell et al. | |
| 2013/0152458 A1 | 6/2013 | Powell et al. | |
| 2014/0117275 A1 | 5/2014 | Chheda et al. | |
| 2014/0117276 A1 | 5/2014 | Komplin et al. | |
| 2014/0117277 A1 | 5/2014 | Denton et al. | |
| 2014/0121418 A1 | 5/2014 | Powell et al. | |
| 2014/0121420 A1 | 5/2014 | Powell et al. | |
| 2014/0121423 A1 | 5/2014 | Johnson et al. | |

FOREIGN PATENT DOCUMENTS

| | | |
|---|---|---|
| EP | 2182047 | 5/2010 |
| FR | 2955118 | 1/2010 |
| FR | 2955118 | 1/2012 |
| WO | 2012060961 | 5/2012 |
| WO | 2012174103 | 12/2012 |
| WO | 2013089798 | 6/2013 |
| WO | 2013089799 | 6/2013 |
| WO | 2014004842 | 1/2014 |
| WO | 2014004844 | 1/2014 |
| WO | 2014004848 | 1/2014 |
| WO | 2014004859 | 1/2014 |
| WO | 2014004867 | 1/2014 |

OTHER PUBLICATIONS

International Search Report for PCT/US2013/066660 dated Mar. 19, 2014.
International Search Report for PCT/US2013/066666 dated Mar. 24, 2014.
International Search Report for PCT/US2013/066631 dated Mar. 19, 2014.
International Search Report for PCT/US2013/066623 dated Mar. 19, 2014.
International Search Report for PCT/US2013/066653 dated Mar. 19, 2014.
International Search Report for PCT/US2013/066625 dated Mar. 19, 2014.
International Search Report for PCT/US2013/066638 dated Dec. 13, 2013.

(Continued)

*Primary Examiner* — Yong Chu
*Assistant Examiner* — Ana Z Muresan

(57) ABSTRACT

Hydrothermal digestion of cellulosic biomass solids may produce a glycol reaction product for subsequent processing. Methods for digesting cellulosic biomass solids to form and process a glycol reaction product may comprise: providing cellulosic biomass solids and a slurry catalyst in a hydrothermal digestion unit, the slurry catalyst being capable of activating molecular hydrogen; heating the cellulosic biomass solids in the hydrothermal digestion unit in the presence of the slurry catalyst, a digestion solvent, and molecular hydrogen, thereby forming a liquor phase comprising soluble carbohydrates; performing a first catalytic reduction reaction on the soluble carbohydrates within the hydrothermal digestion unit, thereby at least partially converting the soluble carbohydrates into a reaction product comprising a glycol; at least partially drying the reaction product, thereby forming a dried reaction product comprising a dried glycol; and at least partially converting the dried glycol into a monohydric alcohol external to the hydrothermal digestion unit.

39 Claims, 2 Drawing Sheets

(56) References Cited

OTHER PUBLICATIONS

International Search Report for PCT/US2013/066642 dated Dec. 13, 2013.
Luo, C. et al., "Cellulose Conversion into Polyols Catalyzed by Reversibly Formed Acids and Supported Ruthenium Clusters in Hot Water", InterScience, Angew. Chem. Int. Ed., 2007 vol. 46, pp. 7637-7639.

Luo, Chen et al., Luo, Chen et al., Cellulose Conversion into Polyols Catalyzed by Reversibly Formed Acids.

ISR—PCT/US2013/066638, International Search Report for PCT/US2013/066638 dated Dec. 12, 2013.

ISR—PCT/US2013/066642, International Search Report for PCT/US2013/066642 dated Dec. 12, 2013.

* cited by examiner

METHODS FOR CONVERSION OF A GLYCOL REACTION PRODUCT OBTAINED FROM HYDROTHERMAL DIGESTION OF CELLULOSIC BIOMASS SOLIDS INTO A DRIED MONOHYDRIC ALCOHOL FEED

The present application claims the benefit of U.S. Provisional Patent Application Ser. No. 61/720,714, filed Oct. 31, 2012 the entire disclosure of which is hereby incorporated by reference.

FIELD OF THE INVENTION

The present disclosure generally relates to digestion of cellulosic biomass solids, and, more specifically, to methods for converting a glycol reaction product obtained in conjunction with hydrothermal digestion of cellulosic biomass solids into a monohydric alcohol feed that can be subsequently processed.

BACKGROUND OF THE INVENTION

A number of substances of commercial significance may be produced from natural sources, including biomass. Cellulosic biomass may be particularly advantageous in this regard due to the versatility of the abundant carbohydrates found therein in various forms. As used herein, the term "cellulosic biomass" refers to a living or recently living biological material that contains cellulose. The lignocellulosic material found in the cell walls of higher plants is the world's largest source of carbohydrates. Materials commonly produced from cellulosic biomass may include, for example, paper and pulpwood via partial digestion, and bioethanol by fermentation.

Plant cell walls are divided into two sections: primary cell walls and secondary cell walls. The primary cell wall provides structural support for expanding cells and contains three major polysaccharides (cellulose, pectin, and hemicellulose) and one group of glycoproteins. The secondary cell wall, which is produced after the cell has finished growing, also contains polysaccharides and is strengthened through polymeric lignin that is covalently crosslinked to hemicellulose. Hemicellulose and pectin are typically found in abundance, but cellulose is the predominant polysaccharide and the most abundant source of carbohydrates. The complex mixture of constituents that is co-present with the cellulose can make its processing difficult, as discussed hereinafter.

Significant attention has been placed on developing fossil fuel alternatives derived from renewable resources. Cellulosic biomass has garnered particular attention in this regard due to its abundance and the versatility of the various constituents found therein, particularly cellulose and other carbohydrates. Despite promise and intense interest, the development and implementation of bio-based fuel technology has been slow. Existing technologies have heretofore produced fuels having a low energy density (e.g., bioethanol) and/or that are not fully compatible with existing engine designs and transportation infrastructure (e.g., methanol, biodiesel, Fischer-Tropsch diesel, hydrogen, and methane). Energy- and cost-efficient processes for processing cellulosic biomass into fuel blends having similar compositions to fossil fuels would be highly desirable to address the foregoing issues and others.

When converting cellulosic biomass into fuel blends and other materials, cellulose and other complex carbohydrates therein can be extracted and transformed into simpler organic molecules, which can be further reformed thereafter. Fermentation is one process whereby complex carbohydrates from cellulosic biomass may be converted into a more usable form. However, fermentation processes are typically slow, require large volume reactors and high dilution conditions, and produce an initial reaction product having a low energy density (ethanol). Digestion is another way in which cellulose and other complex carbohydrates may be converted into a more usable form. Digestion processes can break down cellulose and other complex carbohydrates within cellulosic biomass into simpler, soluble carbohydrates that are suitable for further transformation through downstream reforming reactions. As used herein, the term "soluble carbohydrates" refers to monosaccharides or polysaccharides that become solubilized in a digestion process. Although the underlying chemistry is understood behind digesting cellulose and other complex carbohydrates and further transforming simple carbohydrates into organic compounds reminiscent of those present in fossil fuels, high-yield and energy-efficient digestion processes suitable for converting cellulosic biomass into fuel blends have yet to be developed. Moreover, conventional cellulose digestion processes may produce organic compounds in dilute aqueous solutions (>50% water by weight) that are difficult to further process. The most basic requirement associated with converting cellulosic biomass into fuel blends using digestion and other processes is that the energy input needed to bring about the conversion should not be greater than the available energy output of the product fuel blends. This basic requirement leads to a number of secondary issues that collectively present an immense engineering challenge that has not been solved heretofore.

The issues associated with converting cellulosic biomass into fuel blends in an energy- and cost-efficient manner using digestion are not only complex, but they are entirely different than those that are encountered in the digestion processes commonly used in the paper and pulpwood industry. Since the intent of cellulosic biomass digestion in the paper and pulpwood industry is to retain a solid material (e.g., wood pulp), incomplete digestion is usually performed at low temperatures (e.g., less than about 100° C.) for a fairly short period of time. In contrast, digestion processes suitable for converting cellulosic biomass into fuel blends and other materials are ideally configured to maximize yields by solubilizing as much of the original cellulosic biomass charge as possible in a high-throughput manner.

Production of soluble carbohydrates for use in fuel blends and other materials via routine modification of paper and pulpwood digestion processes is not believed to be economically feasible for a number of reasons. Simply running the digestion processes of the paper and pulpwood industry for a longer period of time to produce more soluble carbohydrates is undesirable from a throughput standpoint. Use of digestion promoters such as strong alkalis, strong acids, or sulfites to accelerate the digestion rate can increase process costs and complexity due to post-processing separation steps and the possible need to protect downstream components from these agents. Accelerating the digestion rate by increasing the digestion temperature can actually reduce yields due to thermal degradation of soluble carbohydrates that can occur at elevated digestion temperatures, particularly over extended periods of time. Once produced by digestion, soluble carbohydrates are very reactive and can rapidly degrade to produce caramelans and other heavy ends degradation products, especially under higher temperature conditions, such as above about 150° C. Use of higher digestion temperatures can also be undesirable from an energy efficiency standpoint. Any of these difficulties can defeat the economic viability of fuel blends derived from cellulosic biomass.

One way in which soluble carbohydrates can be protected from thermal degradation is through subjecting them to one or more catalytic reduction reactions, which may include hydrogenation and/or hydrogenolysis reactions. Stabilizing soluble carbohydrates through conducting one or more catalytic reduction reactions may allow digestion of cellulosic biomass to take place at higher temperatures than would otherwise be possible without unduly sacrificing yields. Depending on the reaction conditions and catalyst used, reaction products formed as a result of conducting one or more catalytic reduction reactions on soluble carbohydrates may comprise one or more alcohol functional groups, particularly including triols, diols, monohydric alcohols, and any combination thereof, some of which may also include a residual carbonyl functionality (e.g., an aldehyde or a ketone). Such reaction products are more thermally stable than soluble carbohydrates and may be readily transformable into fuel blends and other materials through conducting one or more downstream reforming reactions. In addition, the foregoing types of reaction products are good solvents in which a hydrothermal digestion may be performed, thereby promoting solubilization of soluble carbohydrates as their reaction products. By using a digestion solvent containing an alcoholic component, digestion rates may desirably be accelerated and solubilization of cellulosic biomass components such as lignins, for example, may be more effectively promoted. If left unsolubilized or poorly solubilized, lignins and other non-digestible components of cellulosic biomass can sometimes agglomerate and foul process equipment.

More significantly, when the digestion solvent contains components that are synonymous with those that are ultimately produced from the cellulosic biomass, a net energy savings may be realized, since there may be a reduced need to separate the reaction products from the digestion solvent. That is, the reaction product and the components of the digestion solvent may be co-processed with one another in the course of forming a downstream product. When co-processing of the digestion solvent components is not able to be performed, separation and recycling of the digestion solvent can sometimes require input of extensive amounts of energy, which can potentially defeat the viability of fuel blends and other materials derived from cellulosic biomass.

In addition to the desired carbohydrates, other substances may be present within cellulosic biomass that can be especially problematic to deal with in an energy- and cost-efficient manner. Sulfur- and/or nitrogen-containing amino acids or other catalyst poisons may be present in cellulosic biomass. If not removed, these catalyst poisons can impact the catalytic reduction reaction(s) used to stabilize soluble carbohydrates, thereby resulting in process downtime for catalyst regeneration and/or replacement and reducing the overall energy efficiency when restarting the process. On the other hand, in-process removal of these catalyst poisons can also impact the energy efficiency of the biomass conversion process, since the ion-exchange processes typically needed to affect their removal are usually conducted at temperatures below those at which soluble carbohydrates are produced by digestion, thereby introducing heat exchange operations that add to design complexity and may increase operational costs. In addition to catalyst poisons, lignin, which is a non-cellulosic biopolymer, may become solubilized in conjunction with the production of soluble carbohydrates. If not addressed in some manner, lignin concentrations may become sufficiently high during biomass conversion that precipitation eventually occurs, thereby resulting in costly system downtime. In the alternative, some lignin may remain unsolubilized, and costly system downtime may eventually be needed to affect its removal.

Another issue associated with the processing of cellulosic biomass into fuel blends and other materials is created by the need for high conversion percentages of a cellulosic biomass charge into soluble carbohydrates. Specifically, as cellulosic biomass solids are digested, their size gradually decreases to the point that they can become fluidly mobile. As used herein, cellulosic biomass solids that are fluidly mobile, particularly cellulosic biomass solids that are about 3 mm in size or less, will be referred to as "cellulosic biomass fines." Cellulosic biomass fines can be transported out of a digestion zone of a system for converting cellulosic biomass and into one or more zones where solids are unwanted and can be detrimental. For example, cellulosic biomass fines have the potential to plug catalyst beds, transfer lines, valving, and the like. Furthermore, although small in size, cellulosic biomass fines may represent a non-trivial fraction of the cellulosic biomass charge, and if they are not further converted into soluble carbohydrates, the ability to attain a satisfactory conversion percentage may be impacted. Since the digestion processes of the paper and pulpwood industry are run at relatively low cellulosic biomass conversion percentages, smaller amounts of cellulosic biomass fines are believed to be generated and have a lesser impact on those digestion processes.

As evidenced by the foregoing, the efficient conversion of cellulosic biomass into fuel blends and other materials is a complex problem that presents immense engineering challenges. The present disclosure addresses these challenges and provides related advantages as well.

SUMMARY OF THE INVENTION

The present disclosure generally relates to digestion of cellulosic biomass solids, and, more specifically, to methods for converting a glycol reaction product obtained in conjunction with hydrothermal digestion of cellulosic biomass solids into a monohydric alcohol feed that can be subsequently processed.

In some embodiments, the present disclosure provides methods comprising: providing cellulosic biomass solids; converting the cellulosic biomass solids into a reaction product comprising a glycol; at least partially drying the reaction product, thereby forming a dried reaction product comprising a dried glycol; and at least partially converting the dried glycol into a monohydric alcohol.

In some embodiments, the present disclosure provides methods comprising: providing cellulosic biomass solids and a slurry catalyst in a hydrothermal digestion unit, the slurry catalyst being capable of activating molecular hydrogen; heating the cellulosic biomass solids in the hydrothermal digestion unit in the presence of the slurry catalyst, a digestion solvent, and molecular hydrogen, thereby forming a liquor phase comprising soluble carbohydrates; performing a first catalytic reduction reaction on the soluble carbohydrates within the hydrothermal digestion unit, thereby at least partially converting the soluble carbohydrates into a reaction product comprising a glycol; at least partially drying the reaction product, thereby forming a dried reaction product comprising a dried glycol; and at least partially converting the dried glycol into a monohydric alcohol external to the hydrothermal digestion unit.

The features and advantages of the present disclosure will be readily apparent to one having ordinary skill in the art upon a reading of the description of the embodiments that follows.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, as will occur to one having ordinary skill in the art and the benefit of this disclosure.

DETAILED DESCRIPTION

Figure 1:
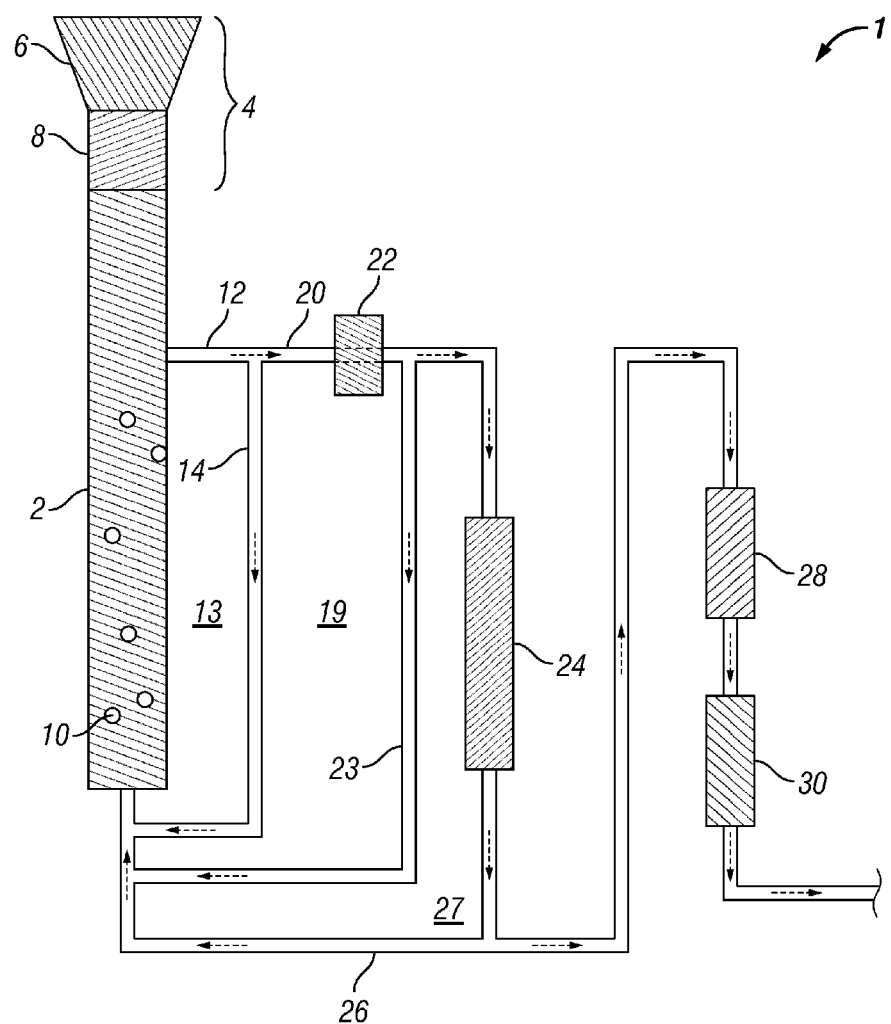
FIG. 1 shows a schematic of an illustrative biomass conversion system in which a glycol reaction product may be produced by an in situ catalytic reduction reaction, dried, converted into a monohydric alcohol, and fed to a reactor housing a condensation catalyst.

The present disclosure generally relates to digestion of cellulosic biomass solids, and, more specifically, to methods for converting a glycol reaction product obtained in conjunction with hydrothermal digestion of cellulosic biomass solids into a monohydric alcohol feed that can be subsequently processed.

In the embodiments described herein, the digestion rate of cellulosic biomass solids may be accelerated in the presence of a digestion solvent. In some instances, the digestion solvent may be maintained at elevated pressures that keep the digestion solvent in a liquid state when raised above its normal boiling point. Although the more rapid digestion rate of cellulosic biomass solids under elevated temperature and pressure conditions may be desirable from a throughput standpoint, soluble carbohydrates may be susceptible to degradation at elevated temperatures, as discussed above.

One way in which the thermal degradation of soluble carbohydrates may be addressed is through conducting the hydrothermal digestion of cellulosic biomass solids in the presence of molecular hydrogen and a slurry catalyst capable of activating the molecular hydrogen (also referred to herein as "hydrogen-activating catalysts" or "hydrocatalytic catalysts"). That is, in such an approach, the hydrothermal digestion of cellulosic biomass solids and the catalytic reduction of soluble carbohydrates produced therefrom may take place in the same vessel. The term "in situ catalytic reduction reaction process" will be used herein to denote a catalytic reduction reaction that takes place in the same vessel as an ongoing hydrothermal digestion. As discussed hereinafter, slurry catalysts may be particularly suitable for use in conjunction with in situ catalytic reduction reaction processes, since slurry catalysts can be readily distributed within a charge of cellulosic biomass solids, thereby allowing soluble carbohydrates to be intercepted and converted into a more stable reaction product as soon as possible after their formation and before they have had an opportunity to significantly degrade. The reaction product may comprise one or more alcohols. As used herein, the term "slurry catalyst" will refer to a catalyst comprising fluidly mobile catalyst particles that can be at least partially suspended in a fluid phase via gas flow, liquid flow, mechanical agitation, or any combination thereof.

In addition to converting soluble carbohydrates into a more stable reaction product, conducting one or more in situ catalytic reduction reactions may also be particularly advantageous from an energy efficiency standpoint. Specifically, the hydrothermal digestion of cellulosic biomass solids is an endothermic process, whereas catalytic reduction reactions are exothermic. Thus, the excess heat generated by the in situ catalytic reduction reaction(s) may be utilized to drive the hydrothermal digestion, thereby lowering the amount of additional heat energy input needed to conduct digestion. Since digestion and catalytic reduction take place in the same vessel in an in situ catalytic reduction reaction process, there is minimal opportunity for heat transfer loss to take place, as would occur if the catalytic reduction reaction(s) were to be conducted in a separate location. In addition, the in situ catalytic reduction reaction(s) may provide a growing supply of the reaction product within the hydrothermal digestion unit, which may serve as and/or replenish the digestion solvent. Under such conditions, there is no express need to separate and recycle the digestion solvent from the reaction product before downstream processing takes place, which may be further advantageous from an energy efficiency standpoint, as discussed above.

Although conducting one or more in situ catalytic reduction reactions may be particularly advantageous from an energy efficiency standpoint and for purposes of stabilizing soluble carbohydrates, successfully executing such a coupled process may be problematic in other aspects. One significant issue that may be encountered is that of adequate catalyst distribution within the digesting cellulosic biomass solids. Without adequate catalyst distribution being realized, ineffective stabilization of soluble carbohydrates may occur as a result of the soluble carbohydrates taking a longer time to reach a catalytic site and undergo catalytic reduction. Although a catalyst might be pre-mixed with cellulosic biomass solids or co-blended with cellulosic biomass solids being added to a hydrothermal digestion unit, these solutions may produce inadequate catalyst distribution and present significant engineering challenges that markedly increase process complexity and operational costs. In contrast, it has been discovered by the present inventors that a slurry catalyst may be effectively distributed within cellulosic biomass solids using fluid flow to convey the slurry catalyst particulates into the interstitial spaces within a charge of cellulosic biomass solids. Although the slurry catalyst may be conveyed into the cellulosic biomass solids using fluid flow from any direction, the inventors consider it most effective to utilize upwardly directed fluid flow for this purpose, as this flow configuration may present a number of advantages. Specifically, it may promote expansion of the cellulosic biomass charge, thereby overcome settling and gravity-induced compaction that occurs during the addition and digestion of cellulosic biomass solids. In addition, by using upwardly directed fluid flow, there may be a reduced need to utilize mechanical stirring or like mechanical agitation techniques that might otherwise be needed to obtain an adequate catalyst distribution. The ability to use no or limited mechanical agitation techniques may allow high loadings of cellulosic biomass solids relative to digestion solvent to be used, thereby improving throughput and process economics.

Suitable techniques for using fluid flow to distribute a slurry catalyst within cellulosic biomass solids are described in commonly owned U.S. Patent Applications 61/665,727 and 61/665,627, each filed on Jun. 28, 2012 (PCT/US2013/048239 and PCT/US2013/048248) and incorporated herein by reference in its entirety. As described therein, cellulosic biomass solids may have at least some innate propensity for retaining a slurry catalyst being conveyed by fluid flow, and at least a portion of the cellulosic biomass solids may be sized to better promote such retention. In addition, using fluid flow to force a slurry catalyst to actively recirculate through a charge of digesting cellulosic biomass solids may ensure adequate catalyst distribution as well as advantageously reduce thermal gradients that may occur during hydrothermal digestion. In addition, active recirculation of the slurry catalyst may address the problem created by the production of cellulosic biomass fines, since they may be co-circulated with the slurry catalyst for continued digestion to take place.

Although conducting one or more in situ catalytic reduction reactions can be highly desirable for stabilizing soluble carbohydrates and achieving heat integration during hydrothermal digestion of cellulosic biomass solids, the catalyst poisons and other substances present therein may make implementing such coupled processes very difficult. One approach that may be used to address this issue is to at least partially remove the catalyst poisons and/or lignin from the cellulosic biomass solids prior to commencing hydrothermal digestion, but such pre-removal techniques can increase process complexity and cost. In the event that catalyst poisons are not removed from the cellulosic biomass solids, a poison-tolerant slurry catalyst may be used to reduce the frequency of catalyst regeneration or replacement. Sulfided catalysts are one class of poison-tolerant catalysts that may be particularly effective for use in this regard. Some examples of sulfided catalysts suitable for use in the present embodiments are discussed in more detail below. Catalysts that are not poison tolerant may also be used to achieve a similar result, but they may need to be regenerated or replaced more frequently than does a poison-tolerant catalyst.

Once a reaction product comprising an alcohol has been produced by conducting a catalytic reduction reaction on soluble carbohydrates, the alcohol may be converted by one or more downstream reforming reactions into other products. In many instances, an initial step of downstream reforming may be a condensation reaction, often conducted in the presence of a condensation catalyst, in which the alcohol or a product formed therefrom is condensed with another molecule to form a higher molecular weight compound. As used herein, the term "condensation reaction" will refer to a chemical transformation in which two or more molecules are coupled with one another to form a carbon-carbon bond in a higher molecular weight compound, usually accompanied by the loss of a small molecule such as water or an alcohol. An illustrative condensation reaction is the Aldol condensation reaction, which will be familiar to one having ordinary skill in the art. Additional disclosure regarding condensation reactions and catalysts suitable for promoting condensation reactions is provided hereinbelow.

Ordinarily, alcohols do not directly undergo condensation reactions, although they are not expressly precluded from doing so. Instead, in order to undergo a condensation reaction, an alcohol is usually converted into a carbonyl compound or a compound that may subsequently react to form a carbonyl compound. The transformation to form the carbonyl compound may take place in concert with the condensation reaction or occur in a discrete conversion prior to the condensation reaction. Suitable transformations for converting alcohols into carbonyl compounds or compounds that may be transformed into carbonyl compounds include, for example, dehydrogenation reactions, dehydration reactions, oxidation reactions, or any combination thereof. When the carbonyl compound is formed catalytically, the same catalyst or a different catalyst than that used to carry out the condensation reaction may be used.

Although a number of different types of catalysts may be used for mediating condensation reactions, zeolite catalysts may be particularly advantageous in this regard. One zeolite catalyst that may be particularly well suited for mediating condensation reactions of alcohols is ZSM-5 (Zeolite Socony Mobil 5), a pentasil aluminosilicate zeolite having a composition of $Na_nAl_nSi_{96-n}O_{192}\cdot16H_2O$ ($0<n<27$), which may transform an alcohol feed into a condensation product. Without being bound by any theory or mechanism, it is believed that this catalyst may promote condensation of alcohols in a concerted manner by mediating a dehydrogenation reaction to produce a carbonyl compound which subsequently undergoes the desired condensation reaction. Other suitable zeolite catalysts may include, for example, ZSM-12, ZSM-22, ZSM-23, SAPO-11, and SAPO-41. Additional types of suitable condensation catalysts are also discussed in more detail herein.

When using zeolite catalysts, it is ordinarily desirable to limit their exposure to water, as the water can incorporate within the zeolite structure and ultimately result in its degradation, particularly under hydrothermal conditions. In addition, when utilizing zeolite catalysts, it is ordinarily desirable to utilize reaction substrates containing only a single alcohol functionality, since more extensively hydroxylated compounds can give rise to undesirable decomposition products due to an increased degree of coking. In light of the foregoing, monohydric alcohols, including monohydric alcohols containing a carbonyl functionality, may be a preferred substrate for condensation reactions mediated by zeolite catalysts. Further, the preferred monohydric alcohols may need to be at least partially dried prior to contacting the catalyst in order to lessen the likelihood of catalyst degradation. Distillation techniques may be used in this regard. A difficulty associated with drying monohydric alcohols through distillation is that azeotropes frequently form, and it may be difficult to remove a significant fraction of the water as a result. Furthermore, the difficulty in removing water from these types of compounds may increase material losses during distillation. Taken together, these issues can be significant enough to jeopardize the viability of cellulosic biomass solids as a feedstock material for production of fuel blends and other materials.

In the course of using a sulfided poison-tolerant catalyst to mediate catalytic reduction reactions of soluble carbohydrates produced via hydrothermal digestion of cellulosic biomass solids, the present inventors observed the production of a high ratio of glycols relative to other products. This result was initially discouraging, given the desirability of monohydric alcohols as substrates for zeolite catalysts, as discussed above. Accordingly, the inventors initially focused on continued reduction of the glycols into monohydric alcohols before subsequently processing the latter compounds. However, it was subsequently recognized that the initial production of glycols from the cellulosic biomass solids could present several process advantages, as discussed hereinafter.

A leading advantage of glycols compared to monohydric alcohols in regard to the techniques described herein is that glycols are much less prone to formation of azeotropes with water. Accordingly, glycols can be dried via distillation much more readily and with a lower degree of material loss than can the corresponding monohydric alcohols. Once dried glycols have been produced by distillation or another suitable drying technique, the dried glycols can thereafter be converted via reduction into monohydric alcohols that contain an amount of water that is comparable to that present in the dried glycols from which they were formed. The dried monohydric alcohols may then be fed to a zeolite catalyst, thereby lessening the difficulties associated with their direct production from cellulosic biomass solids. Thus, proceeding through a glycol intermediate may allow the preferred monohydric alcohols to be produced for use in condensation with much less water present than via their direct formation from cellulosic biomass solids.

Moreover, when drying glycols by distillation, they may be collected as a bottoms product from the distillation vessel due to their high boiling points. Monohydric alcohols and azeotropes thereof, in contrast, are vaporized as an overhead product during distillation. The ability to recover glycols as a bottoms product represents a significant energy advantage for their conversion to biofuels and other materials.

Unless otherwise specified, it is to be understood that use of the terms "biomass" or "cellulosic biomass" in the description herein refers to "cellulosic biomass solids." Solids may be in any size, shape, or form. The cellulosic biomass solids may be natively present in any of these solid sizes, shapes, or forms, or they may be further processed prior to hydrothermal digestion. In some embodiments, the cellulosic biomass solids may be chopped, ground, shredded, pulverized, and the like to produce a desired size prior to hydrothermal digestion. In some or other embodiments, the cellulosic biomass solids may be washed (e.g., with water, an acid, a base, combinations thereof, and the like) prior to hydrothermal digestion taking place.

In practicing the present embodiments, any type of suitable cellulosic biomass source may be used. Suitable cellulosic biomass sources may include, for example, forestry residues, agricultural residues, herbaceous material, municipal solid wastes, waste and recycled paper, pulp and paper mill residues, and any combination thereof. Thus, in some embodiments, a suitable cellulosic biomass may include, for example, corn stover, straw, bagasse, miscanthus, sorghum residue, switch grass, bamboo, water hyacinth, hardwood, hardwood chips, hardwood pulp, softwood, softwood chips, softwood pulp, and any combination thereof. Leaves, roots, seeds, stalks, husks, and the like may be used as a source of the cellulosic biomass. Common sources of cellulosic biomass may include, for example, agricultural wastes (e.g., corn stalks, straw, seed hulls, sugarcane leavings, nut shells, and the like), wood materials (e.g., wood or bark, sawdust, timber slash, mill scrap, and the like), municipal waste (e.g., waste paper, yard clippings or debris, and the like), and energy crops (e.g., poplars, willows, switch grass, alfalfa, prairie bluestream, corn, soybeans, and the like). The cellulosic biomass may be chosen based upon considerations such as, for example, cellulose and/or hemicellulose content, lignin content, growing time/season, growing location/transportation cost, growing costs, harvesting costs, and the like.

Illustrative carbohydrates that may be present in cellulosic biomass solids include, for example, sugars, sugar alcohols, celluloses, lignocelluloses, hemicelluloses, and any combination thereof. Once soluble carbohydrates have been produced through hydrothermal digestion according to the embodiments described herein, the soluble carbohydrates may be transformed into a more stable reaction product comprising a significant fraction of a glycol. As used herein, the term "glycol" will refer to compounds containing two alcohol functional groups, two alcohol functional groups and a carbonyl functionality, or any combination thereof. As used herein, the term "carbonyl functionality" will refer to an aldehyde functionality or a ketone functionality. Cellulosic biomass contains approximately 50% water by weight, and approximately 30% of the dry portion comprises lignin biopolymer. Accordingly, cellulosic biomass solids contain up to about 35 percent by weight cellulosic material (70 percent by weight cellulosic material on a dry basis) that can be converted into soluble carbohydrates and products derived therefrom, including glycols. In some embodiments, at least about 5 percent by weight of the cellulosic biomass solids may be converted into a glycol. In other embodiments, at least about 10 percent by weight of the cellulosic biomass solids may be converted into a glycol. In some embodiments, between about 5% and about 35% of the cellulosic biomass solids by weight may be converted into a glycol, or between about 10% and about 30% of the cellulosic biomass solids by weight, or between about 5% and about 25% of the cellulosic biomass solids by weight, or between about 5% and about 20% of the cellulosic biomass solids by weight, or between about 5% and about 15% of the cellulosic biomass solids by weight, or between about 10% and about 25% of the cellulosic biomass solids by weight, or between about 10% and about 20% of the cellulosic biomass solids by weight, or between about 10% and about 15% of the cellulosic biomass solids by weight Separation and recycle of the glycol may be used to increase the glycol content of the digestion solvent, as discussed hereinafter. For example, in some embodiments, the digestion solvent may comprise between about 10% glycol and about 90% glycol by weight.

Although a glycol may comprise a significant fraction of the reaction product, it is to be recognized that other alcohols, including triols and monohydric alcohols, for example, may also be present. Further, any of these alcohols may additionally include a carbonyl functionality. As used herein, the term "triol" will refer to compounds containing three alcohol functional groups, three alcohol functional groups and a carbonyl functionality, and any combination thereof. As used herein, the term "monohydric alcohol" will refer to compounds containing one alcohol functional group, one alcohol functional group and a carbonyl functionality, and any combination thereof.

As used herein, the term "dried reaction product" refers to a liquor phase that has had a least a portion of the water removed therefrom. Likewise, a "dried glycol" refers to a glycol that has had a least a portion of the water removed therefrom. It is to be recognized that the dried reaction product (dried glycol) need not necessarily be completely anhydrous when dried, simply that its water content be reduced (e.g., less than 50 wt. % water). In some embodiments, the dried glycol may comprise about 40 wt. % or less water. In some or other embodiments, the dried glycol may comprise about 35 wt. % or less water, or about 30 wt. % or less water, or about 25 wt. % or less water, or about 20 wt. % or less water, or about 15 wt. % or less water, or about 10 wt. % or less water, or about 5 wt. % or less water. In some embodiments of the methods described herein, substantially anhydrous glycols may be produced upon drying the reaction product. As used herein, a substance will be considered to be substantially anhydrous if it contains about 5 wt. % water or less.

In some embodiments, methods described herein can comprise: providing cellulosic biomass solids; converting the cellulosic biomass solids into a reaction product comprising a glycol; at least partially drying the reaction product, thereby forming a dried reaction product comprising a dried glycol; and at least partially converting the dried glycol into a monohydric alcohol.

In some embodiments, converting the cellulosic biomass solids into the reaction product may take place in a hydrothermal digestion unit in the presence of a digestion solvent and a slurry catalyst capable of activating molecular hydrogen. In further embodiments, converting the cellulosic biomass solids into a reaction product may further comprise heating the cellulosic biomass solids in the presence of the digestion solvent to form a liquor phase comprising soluble carbohydrates, and performing a first catalytic reduction reaction on the soluble carbohydrates to at least partially form the reaction product. That is, in such embodiments, the reaction product comprising a glycol may be formed via an in situ catalytic reduction reaction process.

Although the reaction product comprising a glycol may be formed via an in situ catalytic reduction reaction process in some embodiments, it is to be recognized that like reaction products may be formed without the catalyst capable of activating molecular hydrogen being present in the same vessel as the cellulosic biomass solids. For example, in some embodiments, soluble carbohydrates in a liquor phase may be produced by a hydrothermal digestion process, and the liquor phase may be transferred to a separate vessel and reacted with molecular hydrogen in the presence of a catalyst capable of activating molecular hydrogen in order to produce a reaction product comprising a glycol. When the catalytic reduction reaction of soluble carbohydrates is conducted in a separate vessel, the catalyst capable of activating molecular hydrogen need not necessarily comprise a slurry catalyst, since catalyst distribution within the digesting cellulosic biomass solids is no longer a concern. That is, the catalyst used for conducting an in situ catalytic reduction reaction process and a catalytic reduction reaction that takes place in a separate vessel need not necessarily be the same.

In some embodiments, methods described herein can comprise: providing cellulosic biomass solids and a slurry catalyst in a hydrothermal digestion unit, the slurry catalyst being capable of activating molecular hydrogen; heating the cellulosic biomass solids in the hydrothermal digestion unit in the presence of the slurry catalyst, a digestion solvent, and molecular hydrogen, thereby forming a liquor phase comprising soluble carbohydrates; performing a first catalytic reduction reaction on the soluble carbohydrates within the hydrothermal digestion unit, thereby at least partially converting the soluble carbohydrates into a reaction product comprising a glycol; at least partially drying the reaction product, thereby forming a dried reaction product comprising a dried glycol; and at least partially converting the dried glycol into a monohydric alcohol external to the hydrothermal digestion unit.

In various embodiments, at least partially drying the reaction product may take place in a location that is separate from that in which the reaction product is formed. That is, in such embodiments, at least partially drying the reaction product comprising a glycol may take place outside the vessel in which the reaction product is formed. For in situ catalytic reduction reaction processes, for example, at least partially drying the reaction product comprising a glycol may take place external to the hydrothermal digestion unit. In such embodiments, the methods described herein may further comprise conveying at least a portion of the reaction product from the hydrothermal digestion unit and at least partially drying the reaction product once conveyed from the hydrothermal digestion unit.

In some embodiments, at least partially drying the reaction product to form a dried glycol may take place external to the hydrothermal digestion unit. In some or other embodiments, at least partially converting the dried glycol into a monohydric alcohol may take place external to the hydrothermal digestion unit. In further embodiments, the methods may further comprise returning at least a portion of the dried glycol to the hydrothermal digestion unit. In some or other further embodiments, the methods may further comprise returning at least a portion of the monohydric alcohol to the hydrothermal digestion unit.

In some embodiments, at least partially drying the reaction product may comprise a distillation to separate water from the glycol in the reaction product. Water present in the reaction product may arise from any source including, for example, the digestion solvent used to conduct hydrothermal digestion, the cellulosic biomass itself, and the catalytic reduction reaction(s) performed in conjunction with stabilizing soluble carbohydrates (e.g., as a product of a hydrogenolysis and/or hydrogenation reaction). In general, glycols have higher boiling points than that of the water being separated from the glycols. For example, ethylene glycol, the smallest glycol, has a boiling point of 197° C., and propylene glycol, has a boiling point of 188° C., each of which is much higher than water's 100° C. boiling point, thereby permitting ready removal of water by distillation techniques to leave behind dried glycols. As described above, glycols are not known to form azeotropes with water, thereby making their separation by distillation more facile than is possible with monohydric alcohols, many of which are known to form binary azeotropes with water. It is to be recognized that other techniques for water removal may be used instead of or in combination with distillation techniques to separate water from the glycol in the reaction product. For example, in some embodiments, the reaction product may be dried through contact with a bed of drying agent such as an anhydrous inorganic salt, molecular sieves, silica gel, alumina, and the like, and/or the dried glycol may be contacted with any of these agents after distillation, if desired, for further drying. In some embodiments, the methods described herein may further comprise separating the dried glycol from the dried reaction product.

In various embodiments, soluble carbohydrates produced from cellulosic biomass solids may be converted into a reaction product comprising a glycol via a catalytic reduction reaction mediated by a catalyst that is capable of activating molecular hydrogen. In some embodiments, the catalytic reduction reaction may take place at a temperature ranging between about 110° C. and about 300° C., or between about 170° C. and about 300° C., or between about 180° C. and about 290° C., or between about 150° C. and about 250° C. In some embodiments, the catalytic reduction reaction may take place at a pH ranging between about 7 and about 13, or between about 10 and about 12. In other embodiments, the catalytic reduction reaction may take place under acidic conditions, such as a pH of about 5 to about 7. In some embodiments, the catalytic reduction reaction may be conducted under a hydrogen partial pressure ranging between about 1 bar (absolute) and about 150 bar, or between about 15 bar and about 140 bar, or between about 30 bar and about 130 bar, or between about 50 bar and about 110 bar. In some embodiments, the catalyst that is capable of activating molecular hydrogen may comprise a slurry catalyst. As described above, slurry catalysts may be particularly desirable for use in conjunction with in situ catalytic reduction reaction processes. For embodiments in which an in situ catalytic reduction reaction process is not used to form a glycol reaction product, any type of catalyst may be used including, for example, slurry catalysts, fixed bed catalysts, ebullating bed catalysts, and the like.

In some embodiments, catalysts capable of activating molecular hydrogen and conducting a catalytic reduction reaction may comprise a metal such as, for example, Cr, Mo, W, Re, Mn, Cu, Cd, Fe, Co, Ni, Pt, Pd, Rh, Ru, Ir, Os, and alloys or any combination thereof, either alone or with promoters such as Au, Ag, Cr, Zn, Mn, Sn, Bi, B, O, and alloys or any combination thereof. In some embodiments, the catalysts and promoters may allow for hydrogenation and hydrogenolysis reactions to occur at the same time or in succession of one another. In some embodiments, such catalysts may also comprise a carbonaceous pyropolymer catalyst containing transition metals (e.g., Cr, Mo, W, Re, Mn, Cu, and Cd) or Group VIII metals (e.g., Fe, Co, Ni, Pt, Pd, Rh, Ru, Ir, and Os). In some embodiments, the foregoing catalysts may be combined with an alkaline earth metal oxide or adhered to a catalytically active support. In some or other embodiments, the catalyst capable of activating molecular hydrogen may be deposited on a catalyst support that is not itself catalytically active.

In some embodiments, the catalyst that is capable of activating molecular hydrogen may comprise a slurry catalyst. In some embodiments, the slurry catalyst may comprise a poison-tolerant catalyst. In some or other embodiments, poison-tolerant catalysts that are not in slurry form may be used, particularly when the reaction product comprising a glycol is not being formed by an in situ catalytic reduction reaction process. As used herein the term "poison-tolerant catalyst" refers to a catalyst that is capable of activating molecular hydrogen without needing to be regenerated or replaced due to low catalytic activity for at least about 12 hours of continuous operation. As discussed above, use of a poison-tolerant catalyst may be particularly desirable when reacting soluble carbohydrates produced from cellulosic biomass solids that have not had catalyst poisons removed therefrom.

In some embodiments, suitable poison-tolerant catalysts may include, for example, a sulfided catalyst. In some or other embodiments, a nitrided catalyst may be used as a poison-tolerant catalyst. Sulfided catalysts suitable for activating molecular hydrogen are described in commonly owned United States Patent Application Publications 2013/0109896, and 2012//0317872, each of which is incorporated herein by reference in its entirety. Sulfiding may take place by treating the catalyst with hydrogen sulfide or an alternative sulfiding agent, optionally while the catalyst is disposed on a solid support. In more particular embodiments, the poison-tolerant catalyst may comprise a sulfided cobalt-molybdate catalyst, such as a catalyst comprising about 1-10 wt. % cobalt oxide and up to about 30 wt. % molybdenum trioxide. In other embodiments, catalysts containing Pt or Pd may also be effective poison-tolerant catalysts for use in the techniques described herein. When mediating in situ catalytic reduction reaction processes, sulfided catalysts may be particularly well suited to form reaction products comprising a substantial fraction of glycols (e.g., $C_2$-$C_6$ glycols) without producing excessive amounts of the corresponding monohydric alcohols. Although poison-tolerant catalysts, particularly sulfided catalysts, may be well suited for forming glycols from soluble carbohydrates, it is to be recognized that other types of catalysts, which may not necessarily be poison-tolerant, may also be used to achieve a like result in alternative embodiments. As will be recognized by one having ordinary skill in the art, various reaction parameters (e.g., temperature, pressure, catalyst composition, introduction of other components, and the like) may be modified to favor the formation of a desired reaction product. Given the benefit of the present disclosure, one having ordinary skill in the art will be able to alter various reaction parameters to change the product distribution obtained from a particular catalyst and set of reactants.

In some embodiments, slurry catalysts suitable for use in the methods described herein may be sulfided by dispersing a slurry catalyst in a fluid phase and adding a sulfiding agent thereto. Suitable sulfiding agents may include, for example, organic sulfoxides (e.g., dimethyl sulfoxide), hydrogen sulfide, salts of hydrogen sulfide (e.g., NaSH), and the like. In some embodiments, the slurry catalyst may be concentrated in the fluid phase after sulfiding, and the concentrated slurry may then be introduced to the cellulosic biomass solids or soluble carbohydrates being produced therefrom. Illustrative techniques for catalyst sulfiding that may be used in conjunction with the methods described herein are described in United States Patent Application Publication No. 20100236988 and incorporated herein by reference in its entirety.

In various embodiments, slurry catalysts used in conjunction with the techniques described herein may have a particulate size of about 250 microns or less. In some embodiments, the slurry catalyst may have a particulate size of about 100 microns or less, or about 10 microns or less. In some embodiments, the minimum particulate size of the slurry catalyst may be about 1 micron. In some embodiments, the slurry catalyst may comprise catalyst fines in the processes described herein. As used herein, the term "catalyst fines" refers to solid catalysts having a nominal particulate size of about 100 microns or less. Catalyst fines may be generated from catalyst production processes, for example, during extrusion of solid catalysts. Catalyst fines may also be produced by grinding larger catalyst solids or during regeneration of catalyst solids. Suitable methods for producing catalyst fines are described in U.S. Pat. Nos. 6,030,915 and 6,127,229, each of which is incorporated herein by reference in its entirety. In some instances, catalyst fines may be intentionally removed from a solid catalyst production run, since they may be difficult to sequester in some catalytic processes. Techniques for removing catalyst fines from larger catalyst solids may include, for example, sieving or like size separation processes. When conducting an in situ catalytic reduction reaction process, catalyst fines may be particularly well suited for use therein, since they can be easily fluidized and distributed in the pore space of the digesting cellulosic biomass solids.

Catalysts that are not particularly poison-tolerant may also be used in conjunction with the techniques described herein. Such catalysts may include, for example, Ru, Pt, Pd, or compounds thereof disposed on a solid support such as, for example, Ru on titanium dioxide or Ru on carbon. Although such catalysts may not have particular poison tolerance, they may be regenerable, such as through exposure of the catalyst to water at elevated temperatures, which may be in a subcritical state or a supercritical state.

In some embodiments, the catalysts used in conjunction with the methods described herein may be operable to generate molecular hydrogen. For example, in some embodiments, catalysts suitable for aqueous phase reforming (i.e., APR catalysts) may be used. Suitable APR catalysts may include, for example, catalysts comprising platinum, palladium, ruthenium, nickel, cobalt, or other Group VIII metals alloyed or modified with rhenium, molybdenum, tin, or other metals. Thus, in some embodiments described herein, an external hydrogen feed may not be needed in order to effectively carry out the stabilization of soluble carbohydrates by a catalytic reduction reaction process. However, in other embodiments, an external hydrogen feed may be used, optionally in combination with internally generated hydrogen.

In various embodiments, the conversion of cellulosic biomass solids into soluble carbohydrates, followed by the subsequent conversion of soluble carbohydrates into a reaction product comprising a glycol, may take place in the presence of a solvent (i.e., a digestion solvent). In various embodiments, the digestion solvent may comprise an organic solvent and water. Although any organic solvent that is at least partially miscible with water may be used in the digestion solvent, particularly advantageous organic solvents are those that can be directly converted into fuel blends and other materials without being separated from the reaction product. That is, particularly advantageous organic solvents may be co-processed with the reaction product and undergo one or more downstream reforming reactions, which may include a condensation reaction, for example. Suitable organic solvents in this regard may include, for example, ethanol, ethylene glycol, propylene glycol, glycerol, and any combination thereof. As one of ordinary skill in the art will recognize, these solvents are all derivable from biological sources, thereby allowing fuel blends and other materials to be produced from cellulosic biomass solids that remain substantially biological in origin, even when co-processed with digestion solvent.

Even more desirably, in some embodiments, the organic solvent may comprise a glycol or be transformable to a glycol under the conditions used for stabilizing soluble carbohydrates. In some embodiments, the digestion solvent may comprise water and glycerol. Glycerol may be a particularly advantageous organic solvent in this regard, since it comprises a good solvent for soluble carbohydrates and readily undergoes a catalytic reduction reaction to form a glycol in the presence of molecular hydrogen and a suitable catalyst. In addition, glycerol is inexpensive and is readily available from natural sources. Thus, in some embodiments, the methods described herein may comprise co-processing a glycol formed from an organic solvent, particularly glycerol, in conjunction with a glycol formed from soluble carbohydrates.

In some embodiments, the digestion solvent may comprise water and a glycol, glycerol, or any combination thereof. In some embodiments, the digestion solvent may further comprise a small amount of a monohydric alcohol. The presence of at least some monohydric alcohols in the digestion solvent may desirably enhance the hydrothermal digestion and/or the catalytic reduction reaction processes being conducted therein. For example, inclusion of about 1% to about 5% by weight monohydric alcohols in the digestion solvent may desirably maintain catalyst activity due to a surface cleaning effect. At higher concentrations of monohydric alcohols, bulk solvent effects may begin to predominate. In some embodiments, the digestion solvent may comprise about 10 wt. % or less monohydric alcohols, with the balance of the digestion solvent comprising water and a glycol, glycerol, or any combination thereof. In some embodiments, the digestion solvent may comprise about 5 wt. % or less monohydric alcohols, or about 4% or less monohydric alcohols, or about 3% or less monohydric alcohols, or about 2% of less monohydric alcohols, or about 1% or less monohydric alcohols. Monohydric alcohols present in the digestion solvent may arise from any source. In some embodiments, the monohydric alcohols may be formed as a co-product with glycols produced from catalytic reduction of soluble carbohydrates. In some or other embodiments, the monohydric alcohols may be produced via a second catalytic reduction reaction conducted subsequent to that used for stabilization of soluble carbohydrates. That is, in such embodiments, the monohydric alcohols may formed from glycols in the reaction product by a catalytic reduction reaction. In such embodiments, the monohydric alcohols may be formed external to the hydrothermal digestion unit and subsequently be returned thereto. In still other embodiments, the monohydric alcohols may be sourced from an external feed and introduced to the hydrothermal digestion unit.

In embodiments in which the digestion solvent further comprises a monohydric alcohol, it may be further desirable to use an entraining agent prior to at least partially drying the reaction product, particularly by distillation. As used herein, the term "entraining agent" refers to a substance that is added to a solvent mixture that substantially reduces the ability of the solvent mixture to form an azeotrope. Use of an entraining agent in conjunction with such digestion solvents may allow the monohydric alcohol to be removed from the glycol reaction product and recovered in a substantially water-free state, at which point the monohydric alcohol may be recycled to the hydrothermal digestion unit, further processed in a condensation reaction, or any combination thereof. In alternative embodiments, the entraining agent may be omitted, and the monohydric alcohol may be separated from the glycol reaction product and recovered in a "wet" state due to formation of a binary or higher azeotrope with water. If desired, the "wet" monohydric alcohol can be recycled to the hydrothermal digestion unit for further use in hydrothermal digestion and catalytic reduction reaction processes. In alternative embodiments, the "wet" monohydric alcohol can simply be discarded, if desired, since the monohydric alcohol comprises but a small volume fraction of the digestion solvent.

In some embodiments, the digestion solvent may comprise between about 1% water and about 99% water, with the organic solvent comprising the balance of the digestion solvent composition. Although higher percentages of water may be more favorable from an environmental standpoint, higher quantities of organic solvent may more effectively promote hydrothermal digestion due to the organic solvent's greater propensity to solubilize carbohydrates and promote catalytic reduction of the soluble carbohydrates. In some embodiments, the digestion solvent may comprise about 90% or less water by weight. In other embodiments, the digestion solvent may comprise about 80% or less water by weight, or about 70% or less water by weight, or about 60% or less water by weight, or about 50% or less water by weight, or about 40% or less water by weight, or about 30% or less water by weight, or about 20% or less water by weight, or about 10% or less water by weight, or about 5% or less water by weight.

In some embodiments, the methods described herein may further comprise removing at least a portion of the liquor phase comprising the reaction product from the hydrothermal digestion unit and thereafter recirculating at least a portion of the liquor phase thereto. In some embodiments, a slurry catalyst used in conjunction with conducting an in situ catalytic reduction reaction process may also be circulated with the liquor phase. In some embodiments, at least a portion of the reaction product may be recirculated to the hydrothermal digestion unit before being at least partially dried. In some or other embodiments, at least a portion of the reaction product may be recirculated to the hydrothermal digestion unit after being at least partially dried. That is, in some embodiments, at least a portion of the dried glycol may be returned to the hydrothermal digestion unit. Recirculation of a dried glycol to the hydrothermal digestion unit may be performed, for example, when it is desired to reduce the quantity of water in the digestion solvent. For example, recirculation of a stream of dried glycols to the hydrothermal digestion unit may be used to adjust the composition of the digestion solvent such that it comprises about 50% or less water by weight in some embodiments, or about 20% or less water by weight in other embodiments.

In some embodiments, heating of the cellulosic biomass solids to form soluble carbohydrates may take place while the hydrothermal digestion unit is in a pressurized state. As used herein, the term "pressurized state" refers to a pressure that is greater than atmospheric pressure (1 bar). Heating a digestion solvent in a pressurized state may allow the normal boiling point of the digestion solvent to be exceeded, thereby allowing the rate of hydrothermal digestion to be increased relative to lower temperature digestion processes. In some embodiments, heating the cellulosic biomass solids in the hydrothermal digestion unit may take place at a pressure of at least about 30 bar. In some embodiments, heating the cellulosic biomass solids in the hydrothermal digestion unit may take place at a pressure of at least about 60 bar, or at a pressure of at least about 90 bar. In some embodiments, heating the cellulosic biomass solids in the hydrothermal digestion unit may take place at a pressure ranging between about 30 bar and about 430 bar. In some embodiments, heating the cellulosic biomass solids in the hydrothermal digestion unit may take place at a pressure ranging between about 50 bar and about 330 bar, or at a pressure ranging between about 70 bar and about 130 bar, or at a pressure ranging between about 30 bar and about 130 bar.

In some embodiments, the cellulosic biomass solids may be maintained at pressure of at least about 30 bar and heated at a temperature of at least about 150° C. In some embodiments, the cellulosic biomass solids may be maintained at a pressure of at least about 70 bar, or at a pressure of least about 100 bar, and heated at a temperature of at least about 150° C. In some or other embodiments, the cellulosic biomass solids may be heated at a temperature of at least about 200° C., or at least about 250° C., or at least about 300° C.

In some embodiments, the hydrothermal digestion unit may be charged with a fixed amount of slurry catalyst, while cellulosic biomass solids are continuously or semi-continuously fed thereto, thereby allowing hydrothermal digestion to take place in a continual manner. That is, fresh cellulosic biomass solids may be added to the hydrothermal digestion unit on a continual or an as-needed basis in order to replenish cellulosic biomass solids that have been digested to form soluble carbohydrates. In some embodiments, the cellulosic biomass solids may be continuously or semi-continuously added to the hydrothermal digestion unit while the hydrothermal digestion unit is in a pressurized state. In some embodiments, the pressurized state may comprise a pressure of at least about 30 bar. Without the ability to introduce fresh cellulosic biomass to a pressurized hydrothermal digestion unit, depressurization and cooling of the hydrothermal digestion unit may take place during biomass addition, significantly reducing the energy- and cost-efficiency of the biomass conversion process. As used herein, the term "continuous addition" and grammatical equivalents thereof will refer to a process in which cellulosic biomass solids are added to a hydrothermal digestion unit in an uninterrupted manner without fully depressurizing the hydrothermal digestion unit. As used herein, the term "semi-continuous addition" and grammatical equivalents thereof will refer to a discontinuous, but as-needed, addition of cellulosic biomass solids to a hydrothermal digestion unit without fully depressurizing the hydrothermal digestion unit. Techniques through which cellulosic biomass solids may be added continuously or semi-continuously to a pressurized hydrothermal digestion unit are discussed in more detail hereinbelow.

In some embodiments, cellulosic biomass solids being continuously or semi-continuously added to the hydrothermal digestion unit may be pressurized before being added to the hydrothermal digestion unit, particularly when the hydrothermal digestion unit is in a pressurized state. Pressurization of the cellulosic biomass solids from atmospheric pressure to a pressurized state may take place in one or more pressurization zones before addition of the cellulosic biomass solids to the hydrothermal digestion unit. Suitable pressurization zones that may be used for pressurizing and introducing cellulosic biomass solids to a pressurized hydrothermal digestion unit are described in more detail in commonly owned United States Patent Application Publications 2013/0152457 and 2013/0152458, and incorporated herein by reference in its entirety. Suitable pressurization zones described therein may include, for example, pressure vessels, pressurized screw feeders, and the like. In some embodiments, multiple pressurization zones may be connected in series to increase the pressure of the cellulosic biomass solids in a stepwise manner.

In various embodiments described herein, a slurry catalyst may be distributed within a charge of cellulosic biomass solids. As used herein, the terms "distribute," "distribution," and variants thereof refer to a condition in which a slurry catalyst is present at all heights of a charge of cellulosic biomass. No particular degree of distribution is implied by use of the term "distribute" or its variants. In some embodiments, the distribution may comprise a substantially homogeneous distribution, such that a concentration of the slurry catalyst is substantially the same at all heights of a cellulosic biomass charge. In other embodiments, the distribution may comprise a heterogeneous distribution, such that different concentrations of the slurry catalyst are present at different heights of the cellulosic biomass charge. When a heterogeneous distribution of the slurry catalyst is present, a concentration of the slurry catalyst within the cellulosic biomass solids may increase from top to bottom in some embodiments or decrease from top to bottom in other embodiments. In some embodiments described herein, fluid flow, particularly upwardly directed fluid flow, may be used to distribute the slurry catalyst within the cellulosic biomass solids. In some embodiments, the velocity of the fluid flow may be used to modulate the type of slurry catalyst distribution obtained.

In some embodiments, the slurry catalyst may be circulated through a fluid circulation loop external to the hydrothermal digestion unit, such that slurry catalyst particulates exiting one end of the charge of cellulosic biomass solids are subsequently reintroduced to the opposite end of the charge. As used herein, the term "circulate" and variants thereof will be used to refer to the condition that exists when at least a portion of a slurry catalyst exits a hydrothermal digestion unit and is subsequently reintroduced thereto one or more times via fluid flow. For example, in embodiments in which upwardly directed fluid flow is used to distribute the slurry catalyst in the cellulosic biomass solids, the slurry catalyst particulates may progress through the cellulosic biomass solids, exit the hydrothermal digestion unit, travel through the fluid circulation loop, and then be reintroduced to or near the bottom of the hydrothermal digestion unit.

In various embodiments, the fluid flow used to distribute the slurry catalyst may be upwardly directed. As discussed above, upwardly directed fluid flow may be particularly efficacious when used for distributing a slurry catalyst within cellulosic biomass solids. In various embodiments, the upwardly directed fluid flow may comprise one or more upwardly directed fluid streams. In various embodiments, the one or more upwardly directed fluid streams may pass through the cellulosic biomass solids, carrying the slurry catalyst thereto, and the one or more upwardly directed fluid streams may subsequently exit the hydrothermal digestion unit. In some embodiments, the upwardly directed fluid flow may comprise one upwardly directed fluid stream. In some embodiments, the upwardly directed fluid flow may comprise two upwardly directed fluid streams, or three upwardly directed fluid streams, or four upwardly directed fluid streams, or five upwardly directed fluid streams. In some embodiments, the one or more upwardly directed fluid streams may comprise a gas stream, a liquid stream, or any combination thereof.

In some embodiments, the one or more upwardly directed fluid streams may comprise a gas stream. For example, in some embodiments, a gas stream being used for upwardly directed fluid flow may comprise a stream of molecular hydrogen. In some or other embodiments, steam, compressed air, or an inert gas such as nitrogen, for example, may be used in place of or in addition to a stream of molecular hydrogen. Up to about 40% steam may be present in the fluid stream in various embodiments. An upwardly directed gas stream may be used to distribute the slurry catalyst within the cellulosic biomass solids when it is desired to maintain the slurry catalyst within the hydrothermal digestion unit and/or when a liquid stream alone is insufficient to distribute the slurry catalyst, for example. Specifically, when it is desired to maintain the slurry catalyst within the hydrothermal digestion unit, a gas stream may convey the slurry catalyst within the cellulosic biomass solids and then exit the hydrothermal digestion, while leaving the slurry catalyst behind at or below the liquid level in the hydrothermal digestion unit.

In some embodiments, the one or more upwardly directed fluid streams may comprise a liquid stream. An upwardly directed liquid stream may be used to distribute the slurry catalyst within the cellulosic biomass solids when it is not necessarily desired to maintain the slurry catalyst within the hydrothermal digestion unit and/or when a gas stream alone is insufficient to distribute the slurry catalyst, for example. Unlike a gas stream, described above, a liquid stream may, in some embodiments, carry the slurry catalyst out of the digestive zone when exiting the hydrothermal digestion unit. For example, in some embodiments, a liquid stream of the digestion solvent may convey the slurry catalyst through the cellulosic biomass solids and into a fluid circulation loop. The fluid circulation loop may then return the cellulosic biomass solids to the hydrothermal digestion unit.

In some embodiments, at least a portion of the slurry catalyst may be fluidly suspended in the digestion solvent by the upwardly directed fluid flow. As used herein, the term "fluidly suspended" refers to the condition that exists when the upwardly directed fluid flow velocity matches the terminal velocity of the slurry catalyst particulates. Accordingly, fluidly suspended slurry catalyst particulates neither sink to the bottom of the hydrothermal digestion unit nor pass completely through the top of a cellulosic biomass charge, carried by the upwardly directed fluid flow. That is, in such embodiments, at least the fluidly suspended slurry catalyst particulates are not circulated through the fluid circulation loop. Attaining a fluidly suspended state for the slurry catalyst may comprise sizing the slurry catalyst particulates to match an intended velocity of upwardly directed fluid flow, adjusting the velocity of upwardly directed fluid flow to match the range of particulate sizes present in a given slurry catalyst, or any combination thereof. Depending on the foregoing factors and others, all of the slurry catalyst particulates may be fluidly suspended in some embodiments, or only a portion of the slurry catalyst particulates may be fluidly suspended in other embodiments. Thus, in some embodiments, at least a portion of the slurry catalyst in the hydrothermal digestion unit may not be circulated through the fluid circulation loop. However, in other embodiments, substantially all of the slurry catalyst particulates may be circulated.

Suitable hydrothermal digestion units configured for circulating a slurry catalyst therethrough are described in commonly owned U.S. Patent Application 61/665,717, filed on Jun. 28, 2012 (PCT/US2013/048212) and incorporated herein by reference in its entirety. For example, in some embodiments, suitable hydrothermal digestion units may comprise a fluid circulation loop that fluidly connects the upper 20% of the hydrothermal digestion unit to the lower 20% of the hydrothermal digestion unit. In some embodiments, the fluid circulation loop may fluidly connect the upper 20% of the hydrothermal digestion unit to the lower 10% of the digestion unit, or the lower 5% of the hydrothermal digestion unit, or the bottom of the hydrothermal digestion unit.

In various embodiments, the first catalytic reduction reaction conducted in the hydrothermal digestion unit may take place in the presence of molecular hydrogen. In some embodiments, the molecular hydrogen may be externally supplied to the hydrothermal digestion unit. For example, in some embodiments, the molecular hydrogen may be supplied with the upwardly directed fluid flow. In some or other embodiments, the molecular hydrogen may be generated internally through use of an aqueous phase reforming (APR) catalyst. Generation of molecular hydrogen using an APR catalyst may take place within the hydrothermal digestion unit in some embodiments or externally in other embodiments.

In addition to circulating the slurry catalyst, the methods described herein may further comprise circulating cellulosic biomass fines through the fluid circulation loop. As described above, the formation of cellulosic biomass fines may ordinarily be problematic when performing complete or near-complete digestion of cellulosic biomass solids due to the opportunity for the cellulosic biomass fines to plug transfer lines, reactor beds, valving, and the like. Since a slurry catalyst is already circulating in some embodiments described herein, the cellulosic biomass fines may be co-flowed with the slurry catalyst particulates, if desired. Specifically, the upwardly directed fluid flow velocity may be adjusted such that the cellulosic biomass fines also become fluidly mobile in the circulating digestion solvent.

In some embodiments, the upwardly directed fluid flow may at least partially expand the cellulosic biomass solids within the hydrothermal digestion unit. At least partial expansion of the cellulosic biomass solids may beneficially ensure good distribution of the slurry catalyst therein and/or reduce the likelihood of blockages occurring in the hydrothermal digestion unit. As used herein the terms "at least partially expand" and "at least partial expansion" refer to a condition that exists in which the packing density of cellulosic biomass solids is reduced by the upwardly directed fluid flow.

Once a dried reaction product comprising a dried glycol has been formed according the embodiments described above, the dried glycol may then be converted into a monohydric alcohol. In some embodiments, conversion of the dried glycol into the monohydric alcohol may take place by a second catalytic reduction reaction in the presence of molecular hydrogen and a catalyst capable of activating the molecular hydrogen. In various embodiments, the monohydric alcohol produced from a dried glycol may also remain substantially free of water or at least contain no more water than the dried glycol from which it is formed, thereby forming a dried monohydric alcohol. The dried monohydric alcohol may then be fed to a condensation catalyst without the difficulties associated with direct production of "wet" monohydric alcohols from soluble carbohydrates.

In some embodiments, the catalyst used for mediating the first catalytic reduction reaction may be the same as the catalyst used for mediating the second catalytic reduction reaction. In other embodiments, different catalysts may be used for mediating the first catalytic reduction reaction and the second catalytic reduction reaction. For example, in some embodiments, a slurry catalyst may be used for forming the reaction product comprising a glycol, and a fixed bed catalyst may be used for forming the monohydric alcohols. In other embodiments, a poison-tolerant catalyst may be used for forming the reaction product comprising a glycol, and a non-poison-tolerant catalyst may be used for forming the monohydric alcohols, particularly if catalyst poisons can be removed from the dried glycol prior to its conversion into the monohydric alcohol. In still other embodiments, a first poison-tolerant catalyst may be used for forming the reaction product comprising a glycol, and a second poison-tolerant catalyst may be used for forming the monohydric alcohol. For example, in some embodiments, a poison-tolerant slurry catalyst may be used to mediate the formation of the reaction product comprising a glycol, and a fixed bed poison-tolerant catalyst may be used to mediate the formation of the monohydric alcohol. In general, any catalyst suitable for performing a catalytic reduction reaction may be used for mediating the transformation of glycols into monohydric alcohols, including those described above.

In some embodiments, the monohydric alcohols produced as described above may comprise a feed for further reforming reactions. In some embodiments, the monohydric alcohol or a product formed therefrom may be exposed to a condensation catalyst and converted into a higher molecular weight compound. In further embodiments, the higher molecular weight compound of the condensation reaction may be further reformed (e.g. into a biofuel) using any combination of further hydrogenolysis reactions and/or hydrogenation reactions, condensation reactions, isomerization reactions, oligomerization reactions, hydrotreating reactions, alkylation reactions, and the like.

In some embodiments, methods described herein may further comprise exposing the monohydric alcohol or a product formed therefrom to a condensation catalyst, and converting the monohydric alcohol into a higher molecular weight compound using the condensation catalyst. The monohydric alcohol may be produced in a reduced-water form by preparing it from a dried reaction product comprising dried glycols, as described above. Particularly when using a zeolite catalyst (e.g., ZSM-5) to mediate a condensation reaction, hydrothermal damage to the zeolite catalyst may be reduced through utilizing a reduced-water monohydric alcohol feed, as described above. As described hereinafter, other condensation catalysts may be suitable as well.

In some embodiments, prior to performing a condensation reaction, a slurry catalyst used in conjunction with mediating at least the first catalytic reduction reaction may be removed from the dried reaction product. Suitable techniques for removing a slurry catalyst from the dried reaction product may include, for example, filtration, membrane separation, separation by centrifugal or centripetal force (e.g., hydroclones and centrifuges), gravity-induced settling, and the like. In some embodiments, slurry catalyst may remain as a residue when a distillation process is used to at least partially dry the reaction product. Separated slurry catalyst may subsequently be returned to the hydrothermal digestion unit, if desired.

In various embodiments, the condensation reaction may take place at a temperature ranging between about 5° C. and about 500° C. The condensation reaction may take place in a condensed phase (e.g., a liquor phase) or in a vapor phase. For condensation reactions taking place in a vapor phase, the temperature may range between about 75° C. and about 500° C., or between about 125° C. and about 450° C. For condensation reactions taking place in a condensed phase, the temperature may range between about 5° C. and about 475° C., or between about 15° C. and about 300° C., or between about 20° C. and about 250° C.

In various embodiments, the higher molecular weight compound produced by the condensation reaction may comprise $\geq C_4$ hydrocarbons. In some or other embodiments, the higher molecular weight compound produced by the condensation reaction may comprise $\geq C_6$ hydrocarbons. In some embodiments, the higher molecular weight compound produced by the condensation reaction may comprise $C_4$-$C_{30}$ hydrocarbons. In some embodiments, the higher molecular weight compound produced by the condensation reaction may comprise $C_6$-$C_{30}$ hydrocarbons. In still other embodiments, the higher molecular weight compound produced by the condensation reaction may comprise $C_4$-$C_{24}$ hydrocarbons, or $C_6$-$C_{24}$ hydrocarbons, or $C_4$-$C_{18}$ hydrocarbons, or $C_6$-$C_{18}$ hydrocarbons, or $C_4$-$C_{12}$ hydrocarbons, or $C_6$-$C_{12}$ hydrocarbons. As used herein, the term "hydrocarbons" refers to compounds containing both carbon and hydrogen without reference to other elements that may be present. Thus, heteroatom-substituted compounds are also described herein by the term "hydrocarbons."

The particular composition of the higher molecular weight compound produced by the condensation reaction may vary depending on the catalyst(s) and temperatures used for both the catalytic reduction reaction and the condensation reaction, as well as other parameters such as pressure. For example, in some embodiments, the product of the condensation reaction may comprise $\geq C_4$ alcohols and/or ketones that are produced concurrently with or in lieu of $\geq C_4$ hydrocarbons. In some embodiments, the $\geq C_4$ hydrocarbons produced by the condensation reaction may contain various olefins in addition to alkanes of various sizes, typically branched alkanes. In still other embodiments, the $\geq C_4$ hydrocarbons produced by the condensation reaction may also comprise cyclic hydrocarbons and/or aromatic compounds. In some embodiments, the higher molecular weight compound produced by the condensation reaction may be further subjected to a catalytic reduction reaction to transform a carbonyl functionality therein to an alcohol and/or a hydrocarbon and to convert olefins into alkanes.

Exemplary compounds that may be produced by a condensation reaction include, for example, $\geq C_4$ alkanes, $\geq C_4$ alkenes, $\geq C_5$ cycloalkanes, $\geq C_5$ cycloalkenes, aryls, fused aryls, $\geq C_4$ alcohols, $\geq C_4$ ketones, and mixtures thereof. The $\geq C_4$ alkanes and $\geq C_4$ alkenes may range from 4 to about 30 carbon atoms (i.e. $C_4$-$C_{30}$ alkanes and $C_4$-$C_{30}$ alkenes) and may be branched or straight chain alkanes or alkenes. The $\geq C_4$ alkanes and $\geq C_4$ alkenes may also include fractions of $C_7$-$C_{14}$, $C_{12}$-$C_{24}$ alkanes and alkenes, respectively, with the $C_7$-$C_{14}$ fraction directed to jet fuel blends, and the $C_{12}$-$C_{24}$ fraction directed to diesel fuel blends and other industrial applications. Examples of various $\geq C_4$ alkanes and $\geq C_4$ alkenes that may be produced by the condensation reaction include, without limitation, butane, butene, pentane, pentene, 2-methylbutane, hexane, hexene, 2-methylpentane, 3-methylpentane, 2,2-dimethylbutane, 2,3-dimethylbutane, heptane, heptene, octane, octene, 2,2,4,-trimethylpentane, 2,3-dimethylhexane, 2,3,4-trimethylpentane, 2,3-dimethylpentane, nonane, nonene, decane, decene, undecane, undecene, dodecane, dodecene, tridecane, tridecene, tetradecane, tetradecene, pentadecane, pentadecene, hexadecane, hexadecene, heptyldecane, heptyldecene, octyldecane, octyldecene, nonyldecane, nonyldecene, eicosane, eicosene, uneicosane, uneicosene, doeicosane, doeicosene, trieicosane, trieicosene, tetraeicosane, tetraeicosene, and isomers thereof.

The $\geq C_5$ cycloalkanes and $\geq C_5$ cycloalkenes may have from 5 to about 30 carbon atoms and may be unsubstituted, mono-substituted or multi-substituted. In the case of mono-substituted and multi-substituted compounds, the substituted group may include a branched $\geq C_3$ alkyl, a straight chain $\geq C_1$ alkyl, a branched $\geq C_3$ alkylene, a straight chain $\geq C_1$ alkylene, a straight chain $\geq C_2$ alkylene, an aryl group, or a combination thereof. In some embodiments, at least one of the substituted groups may include a branched $C_3$-$C_{12}$ alkyl, a straight chain $C_1$-$C_{12}$ alkyl, a branched $C_3$-$C_{12}$ alkylene, a straight chain $C_1$-$C_{12}$ alkylene, a straight chain $C_2$-$C_{12}$ alkylene, an aryl group, or a combination thereof. In yet other embodiments, at least one of the substituted groups may include a branched $C_3$-$C_4$ alkyl, a straight chain $C_1$-$C_4$ alkyl, a branched $C_3$-$C_4$ alkylene, a straight chain $C_1$-$C_4$ alkylene, a straight chain $C_2$-$C_4$ alkylene, an aryl group, or any combination thereof. Examples of $\geq C_5$ cycloalkanes and $\geq C_5$ cycloalkenes that may be produced by the condensation reaction include, without limitation, cyclopentane, cyclopentene, cyclohexane, cyclohexene, methylcyclopentane, methylcyclopentene, ethylcyclopentane, ethylcyclopentene, ethylcyclohexane, ethylcyclohexene, and isomers thereof.

The moderate fractions of the condensation reaction, such as $C_7$-$C_{14}$, may be separated for jet fuel, while heavier fractions, such as $C_{12}$-$C_{24}$, may be separated for diesel use. The heaviest fractions may be used as lubricants or cracked to produce additional gasoline and/or diesel fractions. The $\geq C_4$ compounds may also find use as industrial chemicals, whether as an intermediate or an end product. For example, the aryl compounds toluene, xylene, ethylbenzene, para-xylene, meta-xylene, and ortho-xylene may find use as chemical intermediates for the production of plastics and other products. Meanwhile, $C_9$ aromatic compounds and fused aryl compounds, such as naphthalene, anthracene, tetrahydronaphthalene, and decahydronaphthalene, may find use as solvents or additives in industrial processes.

In some embodiments, a single catalyst may mediate the transformation of a monohydric alcohol into a form suitable for undergoing a condensation reaction as well as mediate the condensation reaction. In other embodiments, a first catalyst may be used to mediate the transformation of the monohydric alcohol into a form suitable for undergoing a condensation reaction, and a second catalyst may be used to mediate the condensation reaction. Unless otherwise specified, it is to be understood that reference herein to a condensation reaction and condensation catalyst refers to either type of condensation process, even if the monohydric alcohol itself is not being directly coupled in the condensation reaction. Further disclosure of suitable condensation catalysts now follows.

In some embodiments, a single catalyst may be used to form a higher molecular weight compound via a condensation reaction of a monohydric alcohol. Without being bound by any theory or mechanism, it is believed that such catalysts may mediate an initial dehydrogenation of the monohydric alcohol, followed by a condensation reaction of the dehydrogenated monohydric alcohol. Zeolite catalysts are one type of catalyst suitable for directly converting dried monohydric alcohols to condensation products in such a manner. A particularly suitable zeolite catalyst in this regard may be ZSM-5, although other zeolite catalysts may also be suitable.

In some embodiments, two catalysts may be used to form a higher molecular weight compound via a condensation reaction of a monohydric alcohol. Without being bound by any theory or mechanism, it is believed that the first catalyst may mediate an initial dehydrogenation of the monohydric alcohol, and the second catalyst may mediate a condensation reaction of the dehydrogenated monohydric alcohol. Like the single-catalyst embodiments discussed previously above, in some embodiments, zeolite catalysts may be used as either the first catalyst or the second catalyst. Again, a particularly suitable zeolite catalyst in this regard may be ZSM-5, although other zeolite catalysts may also be suitable.

Various catalytic processes may be used to form higher molecular weight compounds by a condensation reaction. In some embodiments, the catalyst used for mediating a condensation reaction may comprise a basic site, or both an acidic site and a basic site. Catalysts comprising both an acidic site and a basic site will be referred to herein as multi-functional catalysts. In some or other embodiments, a catalyst used for mediating a condensation reaction may comprise one or more metal atoms. Any of the condensation catalysts may also optionally be disposed on a solid support, if desired.

In some embodiments, the condensation catalyst may comprise a basic catalyst comprising Li, Na, K, Cs, B, Rb, Mg, Ca, Sr, Si, Ba, Al, Zn, Ce, La, Y, Sc, Y, Zr, Ti, hydrotalcite, zinc-aluminate, phosphate, base-treated aluminosilicate zeolite, a basic resin, basic nitride, alloys or any combination thereof. In some embodiments, the basic catalyst may also comprise an oxide of Ti, Zr, V, Nb, Ta, Mo, Cr, W, Mn, Re, Al, Ga, In, Co, Ni, Si, Cu, Zn, Sn, Cd, Mg, P, Fe, or any combination thereof. In some embodiments, the basic catalyst may comprise a mixed-oxide basic catalyst. Suitable mixed-oxide basic catalysts may comprise, for example, Si—Mg—O, Mg—Ti—O, Y—Mg—O, Y—Zr—O, Ti—Zr—O, Ce—Zr—O, Ce—Mg—O, Ca—Zr—O, La—Zr—O, B—Zr—O, La—Ti—O, B—Ti—O, and any combination thereof. In some embodiments, the condensation catalyst may further include a metal or alloys comprising metals such as, for example, Cu, Ag, Au, Pt, Ni, Fe, Co, Ru, Zn, Cd, Ga, In, Rh, Pd, Ir, Re, Mn, Cr, Mo, W, Sn, Bi, Pb, Os, alloys and combinations thereof. Use of metals in the condensation catalyst may be desirable when a dehydrogenation reaction is to be carried out in concert with the condensation reaction. Basic resins may include resins that exhibit basic functionality. The basic catalyst may be self-supporting or adhered to a support containing a material such as, for example, carbon, silica, alumina, zirconia, titania, vanadia, ceria, nitride, boron nitride, a heteropolyacid, alloys and mixtures thereof.

In some embodiments, the condensation catalyst may comprise a hydrotalcite material derived from a combination of MgO and $Al_2O_3$. In some embodiments, the condensation catalyst may comprise a zinc aluminate spinel formed from a combination of ZnO and $Al_2O_3$. In still other embodiments, the condensation catalyst may comprise a combination of ZnO, $Al_2O_3$, and CuO. Each of these materials may also contain an additional metal or alloy, including those more generally referenced above for basic condensation catalysts. In more particular embodiments, the additional metal or alloy may comprise a Group 10 metal such Pd, Pt, or any combination thereof.

In some embodiments, the condensation catalyst may comprise a basic catalyst comprising a metal oxide containing, for example, Cu, Ni, Zn, V, Zr, or any mixture thereof. In some or other embodiments, the condensation catalyst may comprise a zinc aluminate containing, for example, Pt, Pd, Cu, Ni, or any mixture thereof.

In some embodiments, the condensation catalyst may comprise a multi-functional catalyst having both an acidic functionality and a basic functionality. Such condensation catalysts may comprise a hydrotalcite, a zinc-aluminate, a phosphate, Li, Na, K, Cs, B, Rb, Mg, Si, Ca, Sr, Ba, Al, Ce, La, Sc, Y, Zr, Ti, Zn, Cr, or any combination thereof. In further embodiments, the multi-functional catalyst may also include one or more oxides from the group of Ti, Zr, V, Nb, Ta, Mo, Cr, W, Mn, Re, Al, Ga, In, Fe, Co, Ir, Ni, Si, Cu, Zn, Sn, Cd, P, and any combination thereof. In some embodiments, the multi-functional catalyst may include a metal such as, for example, Cu, Ag, Au, Pt, Ni, Fe, Co, Ru, Zn, Cd, Ga, In, Rh, Pd, Ir, Re, Mn, Cr, Mo, W, Sn, Os, alloys or combinations thereof. The basic catalyst may be self-supporting or adhered to a support containing a material such as, for example, carbon, silica, alumina, zirconia, titania, vanadia, ceria, nitride, boron nitride, a heteropolyacid, alloys and mixtures thereof.

In some embodiments, the condensation catalyst may comprise a metal oxide containing Pd, Pt, Cu or Ni. In still other embodiments, the condensation catalyst may comprise an aluminate or a zirconium metal oxide containing Mg and Cu, Pt, Pd or Ni. In still other embodiments, a multi-functional catalyst may comprise a hydroxyapatite (HAP) combined with one or more of the above metals.

In some embodiments, the condensation catalyst may also include a zeolite and other microporous supports that contain Group IA compounds, such as Li, Na, K, Cs and Rb. Preferably, the Group IA material may be present in an amount less than that required to neutralize the acidic nature of the support. A metal function may also be provided by the addition of group VIIIB metals, or Cu, Ga, In, Zn or Sn. In some embodiments, the condensation catalyst may be derived from the combination of MgO and $Al_2O_3$ to form a hydrotalcite material. Another condensation catalyst may comprise a combination of MgO and $ZrO_2$, or a combination of ZnO and $Al_2O_3$. Each of these materials may also contain an additional metal function provided by copper or a Group VIIIB metal, such as Ni, Pd, Pt, or combinations of the foregoing.

The condensation reaction mediated by the condensation catalyst may be carried out in any reactor of suitable design, including continuous-flow, batch, semi-batch or multi-system reactors, without limitation as to design, size, geometry, flow rates, and the like. The reactor system may also use a fluidized catalytic bed system, a swing bed system, fixed bed system, a moving bed system, or a combination of the above. In some embodiments, bi-phasic (e.g., liquid-liquid) and tri-phasic (e.g., liquid-liquid-solid) reactors may be used to carry out the condensation reaction.

In some embodiments, an acid catalyst may be used to optionally dehydrate at least a portion of the reaction product. Suitable acid catalysts for use in the dehydration reaction may include, but are not limited to, mineral acids (e.g., HCl, $H_2SO_4$), solid acids (e.g., zeolites, ion-exchange resins) and acid salts (e.g., $LaCl_3$). Additional acid catalysts may include, without limitation, zeolites, carbides, nitrides, zirconia, alumina, silica, aluminosilicates, phosphates, titanium oxides, zinc oxides, vanadium oxides, lanthanum oxides, yttrium oxides, scandium oxides, magnesium oxides, cerium oxides, barium oxides, calcium oxides, hydroxides, heteropolyacids, inorganic acids, acid modified resins, base modified resins, and any combination thereof. In some embodiments, the dehydration catalyst may also include a modifier. Suitable modifiers may include, for example, La, Y, Sc, P, B, Bi, Li, Na, K, Rb, Cs, Mg, Ca, Sr, Ba, and any combination thereof. The modifiers may be useful, inter alia, to carry out a concerted hydrogenation/dehydrogenation reaction with the dehydration reaction. In some embodiments, the dehydration catalyst may also include a metal. Suitable metals may include, for example, Cu, Ag, Au, Pt, Ni, Fe, Co, Ru, Zn, Cd, Ga, In, Rh, Pd, Ir, Re, Mn, Cr, Mo, W, Sn, Os, alloys, and any combination thereof. The dehydration catalyst may be self supporting, supported on an inert support or resin, or it may be dissolved in a fluid.

The methods described herein will now be described with further reference to the drawings. FIG. 1 shows a schematic of an illustrative biomass conversion system 1 in which a glycol reaction product may be produced by an in situ catalytic reduction reaction, dried, converted into a monohydric alcohol, and fed to a reactor housing a condensation catalyst. As depicted in FIG. 1, cellulosic biomass solids may be introduced to hydrothermal digestion unit 2 via solids introduction mechanism 4. Solids introduction mechanism 4 may comprise loading mechanism 6 and pressure transition zone 8, which may elevate the cellulosic biomass solids from atmospheric pressure to a pressure near that of the operating pressure of hydrothermal digestion unit 2, thereby allowing continuous or semi-continuous introduction of cellulosic biomass solids to take place without fully depressurizing hydrothermal digestion unit 2.

Hydrothermal digestion unit 2 contains slurry catalyst particulates 10 therein. The slurry catalyst particulates are capable of activating molecular hydrogen, such that a catalytic reduction reaction may take place in hydrothermal digestion unit 2. During operation of biomass conversion system 1, the slurry catalyst may mediate a conversion of soluble carbohydrates into a reaction product comprising a glycol within a liquor phase. The liquor phase may exit hydrothermal digestion unit 2 via line 12, carrying some of the slurry catalyst with it. The slurry catalyst may be recirculated to hydrothermal digestion unit 2 via line 14, thereby defining fluid circulation loop 13. Accordingly, recirculated slurry catalyst enters hydrothermal digestion unit 2 in an upflow manner relative to the direction in which the cellulosic biomass solids are introduced thereto.

Liquor phase not returning the slurry catalyst to hydrothermal digestion unit 2 may be transferred via line 20 to drying unit 22. Drying unit 22 may include any suitable technique for at least partially removing water from the liquor phase, thereby producing a dried reaction product comprising dried glycols. As discussed above, suitable techniques for removing water may include, for example, contact with a drying agent or distillation to remove the water. Optionally, at least a portion of the dried glycols may be recirculated to hydrothermal digestion unit 2 via line 23, thereby establishing fluid circulation loop 19.

After at least partially drying the reaction product, the dried glycols may be further transformed into monohydric alcohols in reactor 24. Reactor 24 also contains a catalyst capable of activating molecular hydrogen. Optionally, at least a portion of the monohydric alcohols exiting reactor 24 may be recirculated to hydrothermal digestion unit 2 via line 26, thereby establishing fluid circulation loop 27.

Monohydric alcohols not being recirculated to hydrothermal digestion unit 2 may be further processed via a condensation reaction in one or more reactors. As discussed above, in some embodiments, the monohydric alcohols may first be dehydrogenated before being subjected to condensation. In some embodiments, the dehydrogenation reaction and the condensation reaction may be mediated by the same catalyst. In other embodiments, the dehydrogenation reaction and the condensation reaction may be mediated by different catalysts.

Referring still to FIG. 1, in some embodiments, reactor 28 may contain a catalyst, the catalyst being capable of mediating a dehydrogenation reaction and a condensation reaction. In other embodiments, reactor 28 may contain two or more catalysts, a first catalyst being capable of mediating a dehydrogenation reaction and a second catalyst being capable of mediating a condensation reaction. In the event that two or more catalysts are used in conjunction with performing a condensation process, a first catalyst may be housed in reactor 28 and a second catalyst may be optionally housed in reactor 30, where the condensation reaction takes place in reactor 30.

It is to be recognized that the methods described herein may further comprise conducting additional transformations subsequent to conducting the condensation reaction. Such additional transformations may comprise any combination of further catalytic reduction reactions (e.g., hydrogenation reactions, hydrogenolysis reactions, hydrotreating reactions, and the like), further condensation reactions, isomerization reactions, desulfurization reactions, dehydration reactions, oligomerization reactions, alkylation reactions, and the like. Such transformations may be used to convert the initially produced soluble carbohydrates into a biofuel. Such biofuels may include, for example, gasoline hydrocarbons, diesel fuels, jet fuels, and the like. As used herein, the term "gasoline hydrocarbons" refers to substances comprising predominantly $C_5$-$C_9$ hydrocarbons and having a boiling point of 32° C. to about 204° C. More generally, any fuel blend meeting the requirements of ASTM D2887 may be classified as a gasoline hydrocarbon. Suitable gasoline hydrocarbons may include, for example, straight run gasoline, naphtha, fluidized or thermally catalytically cracked gasoline, VB gasoline, and coker gasoline. As used herein, the term "diesel fuel" refers to substances comprising paraffinic hydrocarbons and having a boiling point ranging between about 187° C. and about 417° C., which is suitable for use in a compression ignition engine. More generally, any fuel blend meeting the requirements of ASTM D975 may also be defined as a diesel fuel. As used herein, the term "jet fuel" refers to substances meeting the requirements of ASTM D1655. In some embodiments, jet fuels may comprise a kerosene-type fuel having substantially $C_8$-$C_{16}$ hydrocarbons (Jet A and Jet A-1 fuels). In other embodiments, jet fuels may comprise a wide-cut or naphtha-type fuel having substantially $C_5$-$C_{15}$ hydrocarbons present therein (Jet B fuels).

To facilitate a better understanding of the present invention, the following examples of preferred embodiments are given. In no way should the following examples be read to limit, or to define, the scope of the invention.

EXAMPLES

Example 1

Formation of a Glycol from Cellulosic Biomass Solids in the Presence of Water Digestion Solvent A 100 mL Parr reactor was charged with 60.16 mL of deionized water, 0.195 grams of potassium carbonate buffer, and 0.754 grams of nickel-oxide promoted cobalt molybdate catalyst was added (DC-2534, Criterion Catalyst Technologies, L.P., containing 1-10% cobalt oxide and molybdenum trioxide (up to 30 wt %) on alumina, and less than 2% nickel). The catalyst was previously sulfided as described in U.S. Patent Application Publication US2010/0236988, which is incorporated herein by reference in its entirety. The reactor was charged with 5.1 grams of southern pine mini-chips (39% moisture) having nominal dimensions of 3 mm×5 mm×5 mm, before pressurizing with 53 bar of hydrogen. The stirred reactor was heated to 190° C. for 1 hour before ramping over 15 minutes to a temperature of 250° C. and holding to complete a 5-hour cycle.

At the end of a reaction cycle, 5 grams of aqueous product were withdrawn via a sample line fitted with a 0.5 micron sintered metal filter, to retain catalyst in the reactor. Approximately 5.0 grams of wood were added to the reactor to initiate another reaction cycle, along with 0.05 to 0.15 grams of buffer as needed to maintain the pH between 5 and 6. This process was repeated over multiple cycles.

After 4 cycles, the reaction product was analyzed by gas chromatography using a 60 m×0.32 mm ID DB-5 column of 1 μm thickness, with 50:1 split ratio, 2 mL/min helium flow, and column oven at 40° C. for 8 minutes, followed by a ramp to 285° C. at 10° C./min, and a hold time of 53.5 minutes. The injector temperature was set at 250° C., and the detector temperature was set at 300° C. A range of alkanes, monooxygenated aldehydes and ketones, glycols, and polyols were observed in the aqueous phase, each with a volatility greater than the $C_6$ sugar alcohol sorbitol. 29.4 wt. % of the observed product yield comprised ethylene glycol and 1,2-propylene glycol, while another 8.8 weight percent comprised glycerol. The reaction sequence was continued through 8 total cycles, at which time the sintered metal filter plugged, and no further samples could be withdrawn from the reactor.

Example 2

Formation of a Glycol from Cellulosic Biomass Solids in the Presence of a Digestion Solvent Comprising Ethylene Glycol, Propylene Glycol, and Water The digestion process of Example 1 was repeated, except the digestion solvent comprised 45% propylene glycol and 5% ethylene glycol in deionized water. In this case, the reaction sequence was repeated over 20 cycles without plugging of the sintered metal filter occurring, thereby showing that greater solubility was achieved in the presence of an organic solvent.

Example 3

Drying in the Presence of a Glycol Solvent

A 75 mL Parr5000 reactor was charged with 18.06 grams of 1,2-propylene glycol, 2.04 grams of ethylene glycol, and 6.74 grams of deionized water to provide a solvent mixture. To this mixture, 0.121 grams of potassium carbonate buffer were added, along with 0.305 grams of the cobalt molybdate catalyst from Example 1. 2.71 grams of soft pine wood mini-chips were added (39% moisture). The reactor was pressurized to 53 bar with hydrogen and heated to 190° C. for 1 hour, followed by heating to 230° C. for 4 hours.

After digestion and reaction, the catalyst and undigested wood were separated by vacuum filtration (Whatman GF/F paper). The filtrate was distilled at atmospheric pressure under a blanket of nitrogen, using a short path microdistillation still with 100 mL catch flask. 4.43 grams of distillate were obtained at a 156.1° C. bottoms temperature and a 98.4° C. tops temperature. The distillate contained only 0.13 grams of measured organics and no detectable glycols. 65% of the initially charged water was removed as distillate. The remaining organics remained as a bottoms phase in the distillation system. This example demonstrates the ease of separation of water from glycols to obtain a glycol concentrate that is at least partially dried, with negligible loss of glycols to the overhead distillate.

Example 4

Conversion of a Glycol Concentrate into Monohydric Alcohols

The dried glycol concentrate from Example 3 was recombined with filtered catalyst and residual undigested wood, and recycled to the Parr5000 reactor. After pressurizing to 52 bar with hydrogen, the temperature was ramped to 190° C. for 1 hour, before heating to 250° C. for 4 hours. Digestion of the wood was more than 98%. 32% of the glycols were converted to monohydric alcohols, including monohydric alcohols containing a ketone functionality.

Example 5

Drying in the Presence of a Monohydric Alcohol Solvent

Example 3 was repeated with 25 wt. % ethanol in deionized water as the digestion solvent. After 6 cycles, the reaction product was distilled as in Example 3. The distillate contained only 40-60% water in addition to monohydric alcohols, indicating the difficulty in removing water from these compounds by distillation.

Examples 6A and 6B

Comparative Acid Condensation Reactions Using ZSM-5 Catalyst

For acid condensation studies, a metal tube reactor 0.5 inch O.D. by 10 inches long was packed with 13.4 gram of ZSM-5 zeolite acid catalyst extrudate (CRI CBV2314) having a silica-alumina ratio (SAR) of 23. The reactor was heated to 375° C. and maintained at a pressure of 100 psi via backpressure control and nitrogen blanket.

Example 6A

A monohydric alcohol-rich feed containing 15 wt. % 2-propanol, 4 wt. % acetone, 3 wt. % acetic acid, 1 wt. % 1,3-propanediol, and 7 wt. % tetrahydrofuran (THF) was vaporized and fed over the ZSM-5 bed at a weight hourly space velocity of 1 gram of feed per gram of catalyst per hour. An aromatics-rich organic product layer containing benzene, toluene, ethylbenzene, xylenes, trimethylbenzenes, naphthalenes, and alkanes greater than $C_3$ was formed at 13-15 wt. % of total product through 3-4 days of operation under these conditions. After 3-4 days of operation, organic layer formation diminished to less than 8%. The ZSM-5 bed was then regenerated via air treatment at 400° C. to remove deposited coke before being placed back on line.

Example 6B

The feed of Example 6A was changed to a mixture of 45 wt. % 1,2-propylene glycol and 5% wt. % ethylene glycol in deionized water, and the temperature was held at 320° C.-375° C. at pressures ranging between 3 and 20 bar. An aromatics-rich organic product layer containing benzene, toluene, ethylbenzene, xylenes, trimethylbenzenes, naphthalenes, and alkanes greater than $C_3$ was formed. Daily regenerations to remove coke formation via burn off in the presence of air at a temperature of 400° C. were needed to sustain the activity of the catalyst, indicating a rate of coke formation that was 3-4 times greater than that observed in Example 6A.

Example 7

Effects of Water on ZSM-5 Catalyst

Effects of water vapor contact with 1% nickel promoted ZSM-5 catalyst having a SAR of 80 was examined via steam treatment of the catalyst at 0, 1, 38 and 52 bar absolute for 3 days. Thereafter, 0.08 grams of the steamed catalyst was packed into the insert of a catalytic pulse microreactor for activity testing in the reversion of tetrahydrofuran (THF) to liquid fuel components. For reversion studies, the microreactor was held at 375° C. The insert was followed by Restek Rtx-1701 (60 m) and DB-5 (60 m) capillary GC columns in series (120 m total length, 0.32 mm ID, 0.25 μm film thickness) for an Agilent/HP 6890 GC equipped with a flame ionization detector. Helium flow was 2.0 mL/min (constant flow mode), with a 10:1 split ratio. The oven temperature for separation of GC components was held at 35° C. for 10 minutes, followed by a ramp to 270° C. at 3° C./min and a 1.67 minute hold time. The detector temperature was 300° C.

Figure 2:
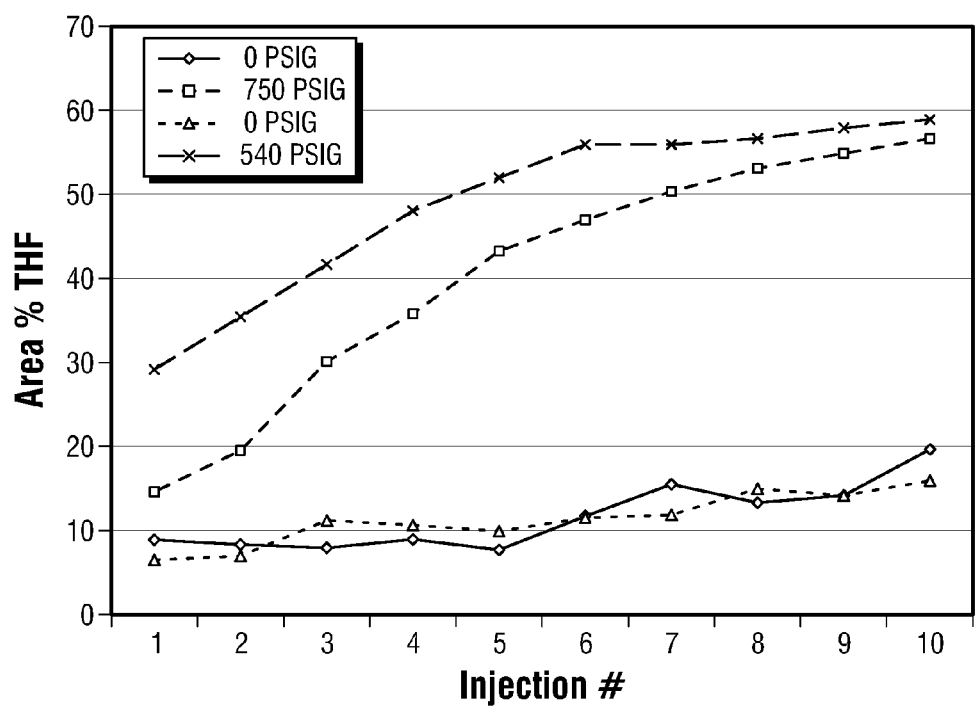
FIG. 2 shows an illustrative plot of THF breakthrough over the course of 10 injections onto untreated and treated ZSM-5 catalyst.

FIG. 2 shows an illustrative plot of THF breakthrough over the course of 10 injections onto untreated and treated ZSM-5 catalyst. THF breakthrough increased significantly for the pressure steamed catalysts, relative to that observed with fresh catalyst or catalysts subjected to steam treatment at ambient pressure, as shown in FIG. 2. These results indicate a deleterious effect of water vapor (steam) on ZSM-5 catalytic activity for synthesis of liquid hydrocarbon products, thereby indicated the desirability of drying the feed prior to condensation.

Example 8

Analysis of Product Distribution

Example 1 was repeated through 4 cycles, except the digestion solvent contained ethanol and the final temperature was only raised to 240° C. After 4 cycles, the product distribution was analyzed by gas chromatography as described above. The product distribution is set forth in Table 1, where percentages are in weight percent of the measured organic portion.

TABLE 1

| Component | Wt. % of Total Organics |
| --- | --- |
| methanol | 8.56 |
| ethanol | n/d |
| acetone | 1.71 |
| isopropanol | 12.20 |
| ethyl acetate | 8.71 |
| acetic acid | 8.71 |
| 1-butanol | n/d |
| ethylene glycol | 13.40 |
| cyclopentanol | 2.09 |
| cyclopentanone | 1.23 |
| propylene glycol | 15.97 |
| methyl cyclopentanone | 1.28 |
| furfuryl alcohol | 6.35 |
| ethyl cyclopentanone | 1.88 |
| pentanediol | 1.58 |
| cyclopentanediol | 4.55 |
| methoxyphenol | 1.45 |
| alkyl methoxyphenol ($C_{10}H_{14}O_2$) | 7.25 |
| $C_5H_{10}O_2$ | 3.09 |
| TOTAL | 100.00 |

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope and spirit of the present invention. The invention illustratively disclosed herein suitably may be practiced in the absence of any element that is not specifically disclosed herein and/or any optional element disclosed herein. While compositions and methods are described in terms of "comprising," "containing," or "including" various components or steps, the compositions and methods may also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces. If there is any conflict in the usages of a word or term in this specification and one or more patent or other documents that may be incorporated herein by reference, the definitions that are consistent with this specification should be adopted.

What is claimed is:

1. A method comprising:
   providing cellulosic biomass solids;
   converting the cellulosic biomass solids into a reaction product comprising a glycol, wherein converting the cellulosic biomass solids into the reaction product takes place in a first reactor in the presence of a digestion solvent comprising about 10% glycol to about 90% glycol by weight and a slurry catalyst capable of activating molecular hydrogen to form a liquor phase comprising soluble carbohydrates;
   performing a first catalytic reduction reaction on the soluble carbohydrates to form the reaction product;
   at least partially drying the reaction product, thereby forming a dried reaction product comprising a dried glycol, wherein the dried glycol comprises about 35 wt. % or less water;
   at least partially converting the dried glycol into a monohydric alcohol in a second reactor via a second catalytic reduction reaction in the presence of a second catalyst capable of activating molecular hydrogen;
   exposing the monohydric alcohol or a product formed therefrom to a condensation catalyst in a third reactor; and
   converting the monohydric alcohol into a higher molecular weight compound using the condensation catalyst.

2. The method of claim 1, wherein at least about 5 percent by weight of the cellulosic biomass solids are converted into the glycol.

3. The method of claim 1, further comprising:
   separating the dried glycol from the dried reaction product.

4. The method of claim 1, wherein the condensation catalyst comprises a zeolite.

5. The method of claim 1, further comprising:
   returning at least a portion of the dried glycol to the hydrothermal digestion unit.

6. The method of claim 1, wherein the slurry catalyst is distributed in the cellulosic biomass solids using fluid flow.

7. The method of claim 6, wherein the slurry catalyst is circulated through a fluid circulation loop external to the hydrothermal digestion unit.

8. The method of claim 1, further comprising:
   removing at least a portion of the liquor phase from the hydrothermal digestion unit and recirculating at least a portion of the removed liquor phase thereto, the removed liquor phase also containing at least a portion of the slurry catalyst.

9. The method of claim 1, further comprising:
   returning at least a portion of the monohydric alcohol to the hydrothermal digestion unit.

10. The method of claim 1, wherein the second catalyst is different than the slurry catalyst.

11. The method of claim 1, wherein the slurry catalyst comprises a poison-tolerant catalyst.

12. The method of claim 11, wherein the poison-tolerant catalyst comprises a sulfided catalyst.

13. The method of claim 1, wherein the digestion solvent comprises an organic solvent and water.

14. The method of claim 13, wherein the organic solvent comprises at least one solvent selected from the group consisting of ethanol, ethylene glycol, propylene glycol, glycerol, and any combination thereof.

15. The method of claim 14, wherein the digestion solvent comprises glycerol and water.

16. The method of claim 15, wherein the digestion solvent further comprises a monohydric alcohol.

17. The method of claim 1, wherein the solvent further comprises water.

18. The method of claim 1, wherein the glycol comprises at least one of ethylene glycol and propylene glycol and the digestion solvent further comprises at least one solvent selected from the group consisting of ethanol, glycerol, and any combination thereof.

19. The method of claim 18, wherein the digestion solvent further comprises glycerol and water.

20. The method of claim 19, wherein the solvent further comprises a monohydric alcohol.

21. The method of claim 1, wherein at least partially drying the reaction product comprises a distillation to separate water from the glycol.

22. A method comprising:
   providing cellulosic biomass solids and a slurry catalyst in a hydrothermal digestion unit, the slurry catalyst being capable of activating molecular hydrogen;
   heating the cellulosic biomass solids in the hydrothermal digestion unit in the presence of the slurry catalyst, a digestion solvent, and molecular hydrogen, thereby forming a liquor phase comprising soluble carbohydrates;
   performing a first catalytic reduction reaction on the soluble carbohydrates within the hydrothermal digestion unit, thereby at least partially converting the soluble carbohydrates into a reaction product comprising a glycol;
   at least partially drying the reaction product, thereby forming a dried reaction product comprising a dried glycol, wherein the dried glycol comprises about 35 wt. % or less water; and
   at least partially converting the dried glycol into a monohydric alcohol external to the hydrothermal digestion unit in a second reaction unit; and
   exposing the monohydric alcohol or a product formed therefrom to a condensation catalyst in a third reaction unit.

23. The method of claim 22, wherein at least about 5 percent by weight of the cellulosic biomass solids are converted into the glycol.

24. The method of claim 22, wherein the dried glycol is at least partially converted into the monohydric alcohol via a second catalytic reduction reaction in the presence of a second catalyst capable of activating molecular hydrogen.

25. The method of claim 24, wherein the second catalyst is different than the slurry catalyst.

26. The method of claim 22, wherein the slurry catalyst is distributed in the cellulosic biomass solids using fluid flow.

27. The method of claim 26, wherein the slurry catalyst is circulated through a fluid circulation loop external to the hydrothermal digestion unit.

28. The method of claim 22, wherein at least partially drying the reaction product comprises a distillation to separate water from the glycol.

29. The method of claim 22, wherein the condensation catalyst comprises a zeolite.

30. The method of claim 22, wherein the slurry catalyst comprises a poison-tolerant catalyst.

31. The method of claim 30, wherein the poison-tolerant catalyst comprises a sulfided catalyst.

32. The method of claim 22, wherein the digestion solvent comprises an organic solvent and water.

33. The method of claim 32, wherein the organic solvent comprises at least one solvent selected from the group consisting of ethanol, ethylene glycol, propylene glycol, glycerol, and any combination thereof.

34. The method of claim 33, wherein the digestion solvent comprises glycerol and water.

35. The method of claim 34, wherein the digestion solvent further comprises a monohydric alcohol.

36. The method of claim 22, further comprising:
removing at least a portion of the liquor phase from the hydrothermal digestion unit and recirculating at least a portion of the removed liquor phase thereto, the removed liquor phase also containing at least a portion of the slurry catalyst.

37. The method of claim 22, further comprising:
returning at least a portion of the monohydric alcohol to the hydrothermal digestion unit.

38. The method of claim 22, wherein at least partially drying the reaction product takes place external to the hydrothermal digestion unit.

39. The method of claim 38, further comprising:
returning at least a portion of the dried glycol to the hydrothermal digestion unit.

* * * * *